(12) United States Patent
Czechtizky et al.

(10) Patent No.: US 8,088,808 B2
(45) Date of Patent: Jan. 3, 2012

(54) SUBSTITUTED N-PHENYL-BIPYRROLIDINE CARBOXAMIDES AND THERAPEUTIC USE THEREOF

(75) Inventors: Werngard Czechtizky, Frankfurt (DE); Zhongli Gao, Flemington, NJ (US); William Joseph Hurst, Oxford, NJ (US); Lothar Schwink, Stadtallendorf (DE); Siegfried Stengelin, Eppstein (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/724,028

(22) Filed: Mar. 15, 2010

(65) Prior Publication Data
US 2010/0173949 A1 Jul. 8, 2010

Related U.S. Application Data

(63) Continuation of application No. PCT/US2008/079757, filed on Oct. 14, 2008.

(60) Provisional application No. 60/980,599, filed on Oct. 17, 2007.

(51) Int. Cl.
*A61K 31/422* (2006.01)
*A61K 31/4025* (2006.01)
*C07D 261/18* (2006.01)
*C07D 403/04* (2006.01)
*C07D 405/14* (2006.01)

(52) U.S. Cl. ......... 514/378; 514/422; 548/248; 548/518

(58) Field of Classification Search ................... 514/341, 514/422, 378, 406, 343; 548/518, 248, 364.1; 546/279.1, 275.4
See application file for complete search history.

(56) References Cited

U.S. PATENT DOCUMENTS
7,223,788 B2   5/2007 Schwink et al.

FOREIGN PATENT DOCUMENTS

| WO | WO 2004/037257 | 5/2004 |
|---|---|---|
| WO | WO 2006/101808 | 9/2006 |
| WO | WO 2006/107661 | 10/2006 |
| WO | WO 2007/005503 | 1/2007 |
| WO | WO 2007/048595 | 5/2007 |
| WO | WO 2009/052063 | 4/2009 |
| WO | WO 2009/052065 | 4/2009 |
| WO | WO 2009/052068 | 4/2009 |

OTHER PUBLICATIONS

Van Der Poel, A. M., et. al., Temporal Patterning of Ultrasonic Distress Calls in the Adult Rat: Effects of Morphine and Benzodiazepines, Psychopharmacology, (1989), vol. 97, pp. 147-148.
Hancock, A. A., et. al. , The Challenge of Drug Discovery of a GPCR Target: Analysis of Preclinical Pharmacology of Histamine H3 Antagonists/Inverse Agonists, Biochemical Pharmacology, vol. 71, (2006), pp. 1103-1113.
Peschke, B., et. al., Cinnamic Amides of (S)-2-(Aminomethyl)Pyrrolidines are Potent H3 Antagonists, Bioorganic & Medicinal Chemistry, vol. 12, (2004), pp. 2603-2616.
Porsalt, R. D., et. al., Depression: A New Animal Model Senstive to Antidepressant Treatments, Nature, vol. 266, pp. 730-732, (1977).
Esbenshade, T. A., et. al., Histamine H3 Receptor Antagonists: Preclinical Promise for treating Obesity and Cognitive Disorders, Molecular Interventions, (2006), vol. 6, No. 2, pp. 77-78.

*Primary Examiner* — Kamal Saeed
*Assistant Examiner* — Kristin Bianchi
(74) *Attorney, Agent, or Firm* — Kelly L. Bender

(57) ABSTRACT

The present invention discloses and claims a series of substituted N-phenyl-bipyrrolidine carboxamides of formula (I).

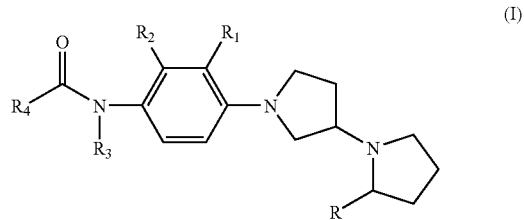

Wherein R, $R_1$, $R_2$, $R_3$ and $R_4$ are as described herein. More specifically, the compounds of this invention are modulators of H3 receptors and are, therefore, useful as pharmaceutical agents, especially in the treatment and/or prevention of a variety of diseases modulated by H3 receptors including diseases associated with the central nervous system. Additionally, this invention also discloses methods of preparation of substituted N-phenyl-bipyrrolidine carboxamides and intermediates therefor.

29 Claims, No Drawings

SUBSTITUTED N-PHENYL-BIPYRROLIDINE CARBOXAMIDES AND THERAPEUTIC USE THEREOF

CROSS REFERENCE TO RELATED APPLICATIONS

This application is a continuation of International application No. PCT/US2008/079,757, filed Oct. 14, 2008, which is incorporated herein by reference in its entirety; which claims the benefit of U.S. Provisional Application No. 60/980,599, filed Oct. 17, 2007.

BACKGROUND OF THE INVENTION

1. Field of the Invention

The present invention relates to a series of substituted N-phenyl-bipyrrolidine carboxamides. The compounds of this invention are modulators of H3 receptors and are, therefore, useful as pharmaceutical agents, especially in the treatment and/or prevention of a variety of diseases modulated by H3 receptors including diseases associated with the central nervous system. Additionally, this invention also relates to methods of preparation of substituted N-phenyl-bipyrrolidine carboxamides and intermediates therefor.

2. Description of the Art

Histamine is a ubiquitous messenger molecule released from mast cells, enterochromaffin-like cells, and neurons. The physiological actions of histamine are mediated by four pharmacologically defined receptors (H1, H2, H3 and H4). All histamine receptors exhibit seven transmembrane domains and are members of the G-protein-coupled receptor superfamily (GPCRs).

The H1 receptor was the first member of the histamine receptor family to be pharmacologically defined, with the development of classical antihistamines (antagonists), such as diphenhydramine and fexofenadine. While antagonism of the H1 receptor of the immune system is commonly used for the treatment of allergic reactions, the H1 receptor is also expressed in various peripheral tissues and the central nervous system (CNS). In the brain, H1 is involved in the control of wakefulness, mood, appetite and hormone secretion.

The H2 receptor is also expressed in the CNS, where it may modulate several processes, including cognition. However, H2 receptor antagonists have primarily been developed to ameliorate gastric ulcers by inhibiting histamine-mediated gastric acid secretion by parietal cells. Classic H2 antagonists include cimetidine, ranitidine, and famotidine.

It should further be noted that H4 receptor function remains poorly defined, but may involve immune regulation and inflammatory processes.

H3 receptors have also been pharmacologically identified in the CNS, heart, lung, and stomach. The H3 receptor differs significantly from other histamine receptors, exhibiting low sequence homology (H1: 22%, H2: 21%, H4: 35%). H3 is a presynaptic autoreceptor on histamine neurons in the brain and a presynaptic heteroreceptor in nonhistamine-containing neurons in both the central and peripheral nervous systems. In addition to histamine, H3 also modulates the release and/or synthesis of other neurotransmitters, including acetylcholine, dopamine, norepinepherin and serotonin. Of particular note, presynaptic modulation of histamine release by H3 allows significant regulation of H1 and H2 receptors in the brain. Modulating multiple neurotransmitter signaling pathways, H3 may contribute to varied physiological processes. Indeed, extensive preclinical evidence indicates that H3 plays a role in cognition, sleep-wake cycle and energy homeostasis.

Modulators of H3 function may be useful in the treatment of obesity and central nervous system disorders (Schizophrenia, Alzheimer's disease, attention-deficit hyperactivity disorder, Parkinson's disease, depression, and epilepsy), sleep disorders (narcolepsy and insomnia), cardiovascular disorders (acute myocardial infarction), respiratory disorders (asthma), and gastrointestinal disorders. See generally, Hancock. Biochem. Pharmacol. 2006 Apr. 14; 71(8):1103-13 and Esbenshade et al. Mol Interv. 2006 April; 6(2):77-88, 59.

Recently, compounds that are somewhat structurally related to the compounds of the present invention have been disclosed to be melanin concentrating hormone (MCH) receptor antagonists, see specifically U.S. Pat. No. 7,223,788. It should however be pointed out that there is no disclosure as to the activity of the compounds disclosed therein at the H3 receptor site.

All of the references described herein are incorporated herein by reference in their entirety.

Accordingly, it is an object of this invention to provide a series of substituted N-phenyl-bipyrrolidine carboxamides as selective H3 receptor ligands for treatment of H3 receptor regulated CNS disorders.

It is also an object of this invention to provide processes for the preparation of the substituted N-phenyl-bipyrrolidine carboxamides as disclosed herein.

Other objects and further scope of the applicability of the present invention will become apparent from the detailed description that follows.

SUMMARY OF THE INVENTION

Surprisingly, it has now been found that the compounds of formula (I) are useful as H3 receptor antagonists and/or inverse agonists. The compounds of formula I are not specifically disclosed, nor exemplified, nor are their activity as H3 receptor antagonists/inverse agonists suggested, in U.S. Pat. No. 7,223,788 as mentioned hereinabove. Moreover, unexpectedly it has now been found that the compounds of formula (I) are selectively active only at H3 receptors and exhibit either low or no activity at the MCH receptor site, which aspect becomes even more apparent from the detailed description that follows.

Thus in accordance with the practice of this invention there is provided a compound of formula (I):

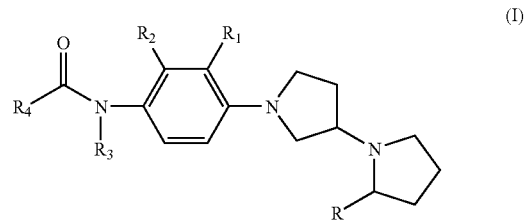

wherein
$R$, $R_1$, $R_2$ and $R_3$ are the same or different and independently of each other chosen from hydrogen, $(C_1-C_4)$alkyl or $CF_3$;
$R_4$ is selected from the group consisting of cyclopropyl, cyclopentyl, cyclohexyl, bicyclo[2,2,1]heptyl, cyclopentylmethyl, tetrahydropyranyl, furanyl, oxazolyl, isoxazolyl and pyrazolyl; wherein said $R_4$ is optionally substituted one or more times with a substituent selected from halogen, methyl, ethyl, pyridinyl, 2-oxo-2H-pyridin-1-yl and $CF_3$.

This invention further includes various salts of the compounds of formula (I) including various enantiomers or diastereomers of compounds of formula (I).

In other aspects of this invention there are also provided various pharmaceutical compositions comprising one or more compounds of formula (I) as well as their therapeutic use in alleviating various diseases which are mediated in-part and/or fully by H3 receptors.

DETAILED DESCRIPTION OF THE INVENTION

The terms as used herein have the following meanings:

As used herein, the expression "$(C_1-C_6)$alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$(C_1-C_4)$alkoxy", "$(C_1-C_4)$thioalkyl" "$(C_1-C_4)$alkoxy$(C_1-C_4)$alkyl", "hydroxy$(C_1-C_4)$alkyl", "$(C_1-C_4)$alkylcarbonyl", "$(C_1-C_4)$alkoxycarbonyl$(C_1-C_4)$alkyl", "$(C_1-C_4)$alkoxycarbonyl", "amino$(C_1-C_4)$alkyl", "$(C_1-C_4)$alkylamino", "$(C_1-C_4)$alkylcarbamoyl$(C_1-C_4)$alkyl", "$(C_1-C_4)$dialkylcarbamoyl$(C_1-C_4)$alkyl" "mono- or di-$(C_1-C_4)$alkylamino$(C_1-C_4)$alkyl", "amino$(C_1-C_4)$alkylcarbonyl" "diphenyl$(C_1-C_4)$alkyl", "phenyl$(C_1-C_4)$alkyl", "phenylcarboyl$(C_1-C_4)$alkyl" and "phenoxy$(C_1-C_4)$alkyl" are to be construed accordingly.

As used herein, the expression "cycloalkyl" includes all of the known cyclic radicals. Representative examples of "cycloalkyl" includes without any limitation cyclopropyl, cyclobutyl, cyclopentyl, cyclohexyl, cycloheptyl, cyclooctyl, and the like. Derived expressions such as "cycloalkoxy", "cycloalkylalkyl", "cycloalkylaryl", "cycloalkylcarbonyl" are to be construed accordingly.

As used herein, the expression "$(C_2-C_6)$alkenyl" includes ethenyl and straight-chained or branched propenyl, butenyl, pentenyl and hexenyl groups. Similarly, the expression "$(C_2-C_6)$alkynyl" includes ethynyl and propynyl, and straight-chained or branched butynyl, pentynyl and hexynyl groups.

As used herein the expression "$(C_1-C_4)$acyl" shall have the same meaning as "$(C_1-C_6)$alkanoyl", which can also be represented structurally as "R—CO—," where R is a $(C_1-C_3)$ alkyl as defined herein. Additionally, "$(C_1-C_3)$alkylcarbonyl" shall mean same as $(C_1-C_4)$acyl. Specifically, "$(C_1-C_4)$acyl" shall mean formyl, acetyl or ethanoyl, propanoyl, n-butanoyl, etc. Derived expressions such as "$(C_1-C_4)$acyloxy" and "$(C_1-C_4)$acyloxyalkyl" are to be construed accordingly.

As used herein, the expression "$(C_1-C_6)$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$(C_1-C_6)$perfluoroalkoxy", is to be construed accordingly.

As used herein, the expression "$(C_6-C_{10})$aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expression, "$(C_6-C_{10})$arylsulfonyl," is to be construed accordingly.

As used herein, the expression "$(C_6-C_{10})$aryl$(C_1-C_4)$alkyl" means that the $(C_6-C_{10})$aryl as defined herein is further attached to $(C_1-C_4)$alkyl as defined herein. Representative examples include benzyl, phenylethyl, 2-phenylpropyl, 1-naphthylmethyl, 2-naphthylmethyl and the like.

As used herein, the expression "heteroaryl" includes all of the known heteroatom containing aromatic radicals. Representative 5-membered heteroaryl radicals include furanyl, thienyl or thiophenyl, pyrrolyl, isopyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, cinnolyl, benzimidazolyl, indazolyl, pyridofuranyl, pyridothienyl, and the like radicals.

As used herein, the expression "heterocycle" includes all of the known reduced heteroatom containing cyclic radicals. Representative 5-membered heterocycle radicals include tetrahydrofuranyl, tetrahydrothiophenyl, pyrrolidinyl, 2-thiazolinyl, tetrahydrothiazolyl, tetrahydrooxazolyl, and the like. Representative 6-membered heterocycle radicals include piperidinyl, piperazinyl, morpholinyl, thiomorpholinyl, and the like. Various other heterocycle radicals include, without limitation, aziridinyl, azepanyl, diazepanyl, diazabicyclo[2.2.1]hept-2-yl, and triazocanyl, and the like.

"Halogen" or "halo" means chloro, fluoro, bromo, and iodo.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, nitric acid, sulfamic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, propionic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

As used herein, the term "prodrug" shall have the generally accepted meaning in the art. One such definition includes a pharmacologically inactive chemical entity that when metabolized or chemically transformed by a biological system such as a mammalian system is converted into a pharmacologically active substance.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

As used herein, 'R' and 'S' are used as commonly used terms in organic chemistry to denote specific configuration of a chiral center. The term 'R' (rectus) refers to that configuration of a chiral center with a clockwise relationship of group priorities (highest to second lowest) when viewed along the bond toward the lowest priority group. The term 'S' (sinister) refers to that configuration of a chiral center with a counter-clockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix 'D' is used to represent the absolute configuration of the isomer in which the functional (determining) group is on the right side of the carbon at the chiral center and 'L', that of the isomer in which it is on the left.

The term "solvate" as used herein means that an aggregate that consists of a solute ion or molecule with one or more solvent molecules. Similarly, a "hydrate" means that a solute ion or molecule with one or more water molecules.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1-6}$alkyl, $(C_2-C_6)$alkenyl, $(C_1-C_6)$perfluoroalkyl, phenyl, hydroxy, —$CO_2H$, an ester, an amide, $(C_1-C_6)$alkoxy, $(C_1-C_6)$thioalkyl, $(C_1-C_6)$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

"Therapeutically effective amount" means an amount of the compound which is effective in treating the named disease, disorder or condition.

The term "treating" refers to:
(i) preventing a disease, disorder or condition from occurring in a patient that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

Thus, in accordance with the practice of this invention there is provided a compound of the formula I:

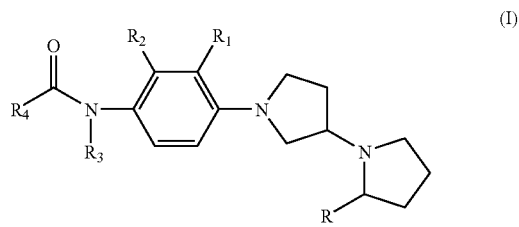

(I)

wherein
R, $R_1$, $R_2$ and $R_3$ are the same or different and independently of each other chosen from hydrogen, $(C_1-C_4)$alkyl or $CF_3$;
$R_4$ is selected from the group consisting of cyclopropyl, cyclopentyl, cyclohexyl, bicyclo[2,2,1]heptyl, cyclopentylmethyl, tetrahydropyranyl, furanyl, oxazolyl, isoxazolyl and pyrazolyl; wherein said $R_4$ is optionally substituted one or more times with a substituent selected from halogen, methyl, ethyl, pyridinyl, 2-oxo-2H-pyridin-1-yl and $CF_3$.

This invention further includes various salts of the compounds of formula (I) including various enantiomers or diastereomers of compounds of formula (I). As noted hereinabove and by way of specific examples hereafter all of the salts that can be formed including pharmaceutically acceptable salts are part of this invention. As also noted hereinabove and hereafter all of the conceivable enantiomeric and diastereomeric forms of compounds of formula (I) are part of this invention.

In one of the embodiments, the compounds of formula (I) wherein R is methyl; $R_2$ is methyl or $CF_3$; $R_1$ and $R_3$ are hydrogen are disclosed hereinbelow.

In another embodiment of this invention there is also provided a compound of formula (I), wherein R and $R_1$ are methyl; $R_2$ and $R_3$ are hydrogen.

In yet another embodiment of this invention there is disclosed a compound of formula (I), wherein $R_4$ is selected from cyclopropyl, cyclopentyl, cyclohexyl or bicyclo[2.2.1]heptane, which are optionally substituted one or more times with methyl.

In a further embodiment of this invention there is provided a compound of formula (I), wherein $R_4$ is tetrahydropyranyl.

In one of the embodiments of this invention there is also disclosed a compound of formula (I), wherein $R_4$ is selected from furanyl, oxazolyl, isoxazolyl and pyrazolyl, which are optionally substituted one or more times with methyl.

In yet another embodiment of this invention there is provided a compound of formula (I), wherein $R_4$ is selected from isoxazolyl or isoxazolyl substituted one or more times with methyl.

In a further aspect of this invention the following compounds encompassed by the scope of this invention without any limitation may be enumerated:
cyclopropanecarboxylic acid [2-methyl-4-(2-methyl-[1,3']bipyrrolidinyl-1'-yl)-phenyl]-amide;

cyclopropanecarboxylic acid [4-(2-methyl-[1,3']bipyrrolidinyl-1'-yl)-2-trifluoromethyl-phenyl]-amide;
cyclopropanecarboxylic acid [4-(2-methyl-[1,3']bipyrrolidinyl-1'-yl)-phenyl]-amide;
cyclopropanecarboxylic acid [3-methyl-4-(2-methyl-[1,3'] bipyrrolidinyl-1'-yl)-phenyl]-amide;
2,2,3,3-tetramethyl-cyclopropanecarboxylic acid [2-methyl-4-(2(S)-methyl-[1,3'(S)]bipyrrolidinyl-1'-yl)-phenyl]-amide;
2,2,3,3-tetramethyl-cyclopropanecarboxylic acid [2-methyl-4-(2-methyl-[1,3']bipyrrolidinyl-1'-yl)-phenyl]-amide;
2,2,3,3-tetramethyl-cyclopropanecarboxylic acid [4-(2-methyl-[1,3']bipyrrolidinyl-1'-yl)-phenyl]-amide;
2,2,3,3-tetramethyl-cyclopropanecarboxylic acid [3-methyl-4-(2-methyl-[1,3']bipyrrolidinyl-1'-yl)-phenyl]-amide;
cyclopentanecarboxylic acid [2-methyl-4-(2(S)-methyl-[1,3'(S)]bipyrrolidinyl-1'-yl)-phenyl]-amide;
cyclohexanecarboxylic acid [2-methyl-4-(2S-methyl-[1,3'S]bipyrrolidinyl-1'-yl)-phenyl]-amide;
2-cyclopentyl-N-[2-methyl-4-(2-methyl-[1,3']bipyrrolidinyl-1'-yl)-phenyl]-acetamide;
2-cyclopentyl-N-[2-methyl-4-(2(S)-methyl-[1,3'(S)]bipyrrolidinyl-1'-yl)-phenyl]-acetamide;
2-cyclopentyl-N-[4-(2-methyl-[1,3']bipyrrolidinyl-1'-yl)-phenyl]-acetamide;
2-cyclopentyl-N-[3-methyl-4-(2-methyl-[1,3']bipyrrolidinyl-1'-yl)-phenyl]-acetamide; bicyclo[2.2.1]heptane-2-carboxylic acid [2-methyl-4-(2S-methyl-[1,3'S]bipyrrolidinyl-1'-yl)-phenyl]-amide;
(1S,4R)-bicyclo[2.2.1]heptane-2-carboxylic acid [2-methyl-4-(2-methyl-[1,3']bipyrrolidinyl-1'-yl)-phenyl]-amide;
(1S,4R)-bicyclo[2.2.1]heptane-2-carboxylic acid [3-methyl-4-(2-methyl-[1,3']bipyrrolidinyl-1'-yl)-phenyl]-amide;
(1S,4R)-bicyclo[2.2.1]heptane-2-carboxylic acid [4-(2-methyl-[1,3']bipyrrolidinyl-1'-yl)-phenyl]-amide;
tetrahydro-pyran-4-carboxylic acid [2-methyl-4-(2(2S)-methyl-[1,3'(3'S)]bipyrrolidinyl-1'-yl)-phenyl]-amide;
tetrahydro-pyran-4-carboxylic acid [4-(2-methyl-[1,3']bipyrrolidinyl-1'-yl)-phenyl]-amide;
tetrahydro-pyran-4-carboxylic acid [3-methyl-4-(2-methyl-[1,3']bipyrrolidinyl-1'-yl)-phenyl]-amide;
tetrahydro-pyran-4-carboxylic acid [2-methyl-4-(2-methyl-[1,3']bipyrrolidinyl-1'-yl)-phenyl]-amide;
furan-3-carboxylic acid [2-methyl-4-(2S-methyl-[1,3'S]bipyrrolidinyl-1'-yl)-phenyl]-amide;
furan-2-carboxylic acid [2-methyl-4-(2(S)-methyl-[1,3'(S)]bipyrrolidinyl-1'-yl)-phenyl]-amide;
5-(2-oxo-2H-pyridin-1-yl)-furan-2-carboxylic acid [2-methyl-4-(2-methyl-[1,3]bipyrrolidinyl-1'-yl)-phenyl]-amide;
2-methyl-oxazole-4-carboxylic acid [2-methyl-4-(2(S)-methyl-[1,3'(S)]bipyrrolidinyl-1'-yl)-phenyl]-amide;
3-methyl-isoxazole-5-carboxylic acid [2-methyl-4-(2S-methyl-[1,3'S]bipyrrolidinyl-1'-yl)-phenyl]-amide;
3,5-dimethyl-isoxazole-4-carboxylic acid [2-methyl-4-(2(2S)-methyl-[1,3'(3'S)]bipyrrolidinyl-1'-yl)-phenyl]-amide;
3,5-dimethyl-isoxazole-4-carboxylic acid [3-methyl-4-(2-methyl-[1,3']bipyrrolidinyl-1'-yl)-phenyl]-amide;
3,5-dimethyl-isoxazole-4-carboxylic acid [2-methyl-4-(2-methyl-[1,3']bipyrrolidinyl-1'-yl)-phenyl]-amide;
3,5-dimethyl-isoxazole-4-carboxylic acid [4-(2-methyl-[1,3']bipyrrolidinyl-1'-yl)-phenyl]-amide;
1H-pyrazole-4-carboxylic acid [4-(2-methyl-[1,3']bipyrrolidinyl-1'-yl)-phenyl]-amide;
1H-pyrazole-4-carboxylic acid [2-methyl-4-(2-methyl-[1,3'] bipyrrolidinyl-1'-yl)-phenyl]-amide;
1H-pyrazole-4-carboxylic acid [3-methyl-4-(2-methyl-[1,3'] bipyrrolidinyl-1'-yl)-phenyl]-amide;
5-methyl-1H-pyrazole-3-carboxylic acid [2-methyl-4-(2(2S)-methyl-[1,3'(3'S)]bipyrrolidinyl-1'-yl)-phenyl]-amide;
5-methyl-1H-pyrazole-3-carboxylic acid [2-methyl-4-(2-methyl-[1,3']bipyrrolidinyl-1'-yl)-phenyl]-amide;
5-methyl-1H-pyrazole-3-carboxylic acid [3-methyl-4-(2-methyl-[1,3']bipyrrolidinyl-1'-yl)-phenyl]-amide;
5-methyl-1H-pyrazole-3-carboxylic acid [4-(2-methyl-[1,3'] bipyrrolidinyl-1'-yl)-phenyl]-amide;
5-methyl-1H-pyrazole-3-carboxylic acid [4-(2-methyl-[1,3'] bipyrrolidinyl-1'-yl)-2-trifluoromethyl-phenyl]-amide;
1,5-dimethyl-1H-pyrazole-3-carboxylic acid [2-methyl-4-(2(2S)-methyl-[1,3'(3'S)]bipyrrolidinyl-1'-yl)-phenyl]-amide; and
5-pyridin-4-yl-2H-pyrazole-3-carboxylic acid [2-methyl-4-(2-methyl-[1,3']bipyrrolidinyl-1'-yl)-phenyl]-amide.

All of the above compounds may also include corresponding salts wherever possible including the pharmaceutically acceptable salts thereof.

In another aspect of this invention the following compounds encompassed by compound of formula (I) of this invention without any limitation may be enumerated:
cyclopropanecarboxylic acid [2-methyl-4-(2-methyl-[1,3'] bipyrrolidinyl-1'-yl)-phenyl]-amide;
2-cyclopentyl-N-[2-methyl-4-(2-methyl-[1,3']bipyrrolidinyl-1'-yl)-phenyl]-acetamide;
cyclohexanecarboxylic acid [2-methyl-4-(2S-methyl-[1,3'S] bipyrrolidinyl-1'-yl)-phenyl]-amide;
bicyclo[2.2.1]heptane-2-carboxylic acid [2-methyl-4-(2S-methyl-[1,3'S]bipyrrolidinyl-1'-yl)-phenyl]-amide;
tetrahydro-pyran-4-carboxylic acid [2-methyl-4-(2(2S)-methyl-[1,3'(3'S)]bipyrrolidinyl-1'-yl)-phenyl]-amide;
tetrahydro-pyran-4-carboxylic acid [4-(2-methyl-[1,3']bipyrrolidinyl-1'-yl)-phenyl]-amide;
furan-3-carboxylic acid [2-methyl-4-(2S-methyl-[1,3'S]bipyrrolidinyl-1'-yl)-phenyl]-amide;
3-methyl-isoxazole-5-carboxylic acid [2-methyl-4-(2S-methyl-[1,3'S]bipyrrolidinyl-1'-yl)-phenyl]-amide;
3,5-dimethyl-isoxazole-4-carboxylic acid [2-methyl-4-(2(2S)-methyl-[1,3'(3'S)]bipyrrolidinyl-1'-yl)-phenyl]-amide; and
3,5-dimethyl-isoxazole-4-carboxylic acid [3-methyl-4-(2-methyl-[1,3']bipyrrolidinyl-1'-yl)-phenyl]-amide.

Again all of the conceivable salts of the above noted compounds including the pharmaceutically acceptable salts are part of this invention.

In a further aspect of this invention the following compounds within the scope of this invention may be enumerated:
cyclohexanecarboxylic acid [2-methyl-4-(2S-methyl-[1,3'S] bipyrrolidinyl-1'-yl)-phenyl]-amide;
bicyclo[2.2.1]heptane-2-carboxylic acid [2-methyl-4-(2S-methyl-[1,3'S]bipyrrolidinyl-1'-yl)-phenyl]-amide;
tetrahydro-pyran-4-carboxylic acid [2-methyl-4-(2(2S)-methyl-[1,3'(3'S)]bipyrrolidinyl-1'-yl)-phenyl]-amide; and
3,5-dimethyl-isoxazole-4-carboxylic acid [2-methyl-4-(2(2S)-methyl-[1,3'(3'S)]bipyrrolidinyl-1'-yl)-phenyl]-amide.

Again all of the conceivable salts of the above noted compounds including the pharmaceutically acceptable salts are part of this invention.

In another aspect of this invention the compound of this invention may be represented by a specific stereoisomeric form of formula (II):

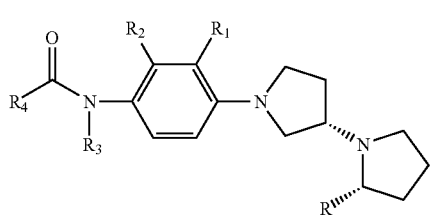

(II)

wherein R, $R_1$, $R_2$, $R_3$ and $R_4$ are as defined hereinabove.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein. For instance, as stated hereinabove a few of the structurally similar compounds have been disclosed in U.S. Pat. No. 7,223,788. Also, see R. C. Larock, "Comprehensive Organic Transformations," VCH publishers, 1989.

It is also well known that in various organic reactions it may be necessary to protect reactive functional groups, such as for example, amino groups, to avoid their unwanted participation in the reactions. Conventional protecting groups may be used in accordance with standard practice and known to one of skilled in the art, for example, see T. W. Greene and P. G. M. Wuts in "Protective Groups in Organic Chemistry" John Wiley and Sons, Inc., 1991. For example, suitable amine protecting groups include without any limitation sulfonyl (e.g., tosyl), acyl (e.g., benzyloxycarbonyl or t-butoxycarbonyl) and arylalkyl (e.g., benzyl), which may be removed subsequently by hydrolysis or hydrogenation as appropriate. Other suitable amine protecting groups include trifluoroacetyl [—C(=O)CF$_3$] which may be removed by base catalyzed hydrolysis, or a solid phase resin bound benzyl group, such as a Merrifield resin bound 2,6-dimethoxybenzyl group (Ellman linker) or a 2,6-dimethoxy-4-[2-(polystyrylmethoxy)ethoxy]benzyl, which may be removed by acid catalyzed hydrolysis, for example with TFA.

More specifically, the compounds disclosed herein and various precursors used therefor can be synthesized according to the following procedures of Schemes 1-, wherein the R, $R_1$, $R_2$, $R_3$ and $R_4$ are as defined for Formula I unless otherwise indicated.

For instance, Scheme 1 illustrates the preparation of the intermediate [1,3']-pyrrolidinyl-pyrrolidine of formula (4), wherein R is as defined herein. First, in step 1, Scheme 1, suitably protected (for example tert-butyloxycarbonyl (boc)) pyrrolidinone of formula (1) is condensed with a desired substituted pyrrolidine of formula (2) by any of the known reductive amination procedures to from an intermediate of formula (3). For instance, such condensation reactions are generally carried out in the presence of reducing agents such as triacetoxyborohydride in an inert atmosphere, such as nitrogen atmosphere. The reaction can be carried out either at sub-ambient, ambient or super-ambient reaction temperatures and pressures. Typically, such reactions are carried out at room temperature at atmospheric pressure of nitrogen. The reaction mixture is then worked-up using procedures known to skilled in the art to isolate the intermediate of formula (3).

In step 2, Scheme 1, the intermediate (3) is then de-protected to form the desired [1,3]-pyrrolidinyl-pyrrolidine of formula (4). Such deprotection reactions are generally carried out under acidic conditions, for example, in the presence of hydrochloric acid at sub-ambient to ambient temperatures, for example in the temperature range of about –10° C. to room temperature. However, other suitable reaction temperatures can also be used depending upon the nature of the intermediate of formula (3).

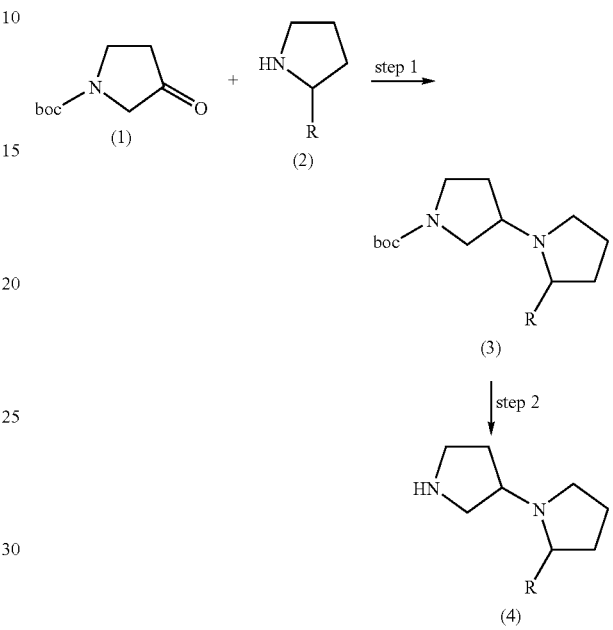

Scheme 2 illustrates preparation of enantiomerically pure isomers of the [1,3']pyrrolidinyl-pyrrolidine of formula (9), wherein R is as defined herein. In step 1, Scheme 2, suitably protected (for example boc) pyrrolidine alcohol of formula (5) is treated with p-toluene sulfonyl chloride to form intermediate of formula (6). This reaction can be carried out using any of the procedures known to one skilled in the art, such as for example carrying out the reaction in the presence of a suitable base such as triethylamine and DMAP in a suitable organic solvent, preferably an aprotic solvent such as dichloromethane at sub-ambient or ambient temperature conditions.

In step 2, Scheme 2, the intermediate of formula (6) is condensed with a desired pyrrolidine of formula (7). Again, such condensation reactions can be carried out using any of the procedures known to one skilled in the art in order to obtain the intermediate of formula (8). Typically, such condensation reactions are carried out in the presence of a base such as potassium carbonate in the presence of solvents such as acetonitrile at ambient to super-ambient temperature conditions.

In step 3, Scheme 2, the intermediate of formula (8) is then reacted with an acid, such as hydrochloric acid in a suitable solvent, such as dioxane, to form the desired stereospecific isomer of [1,3']pyrrolidinyl-pyrrolidine intermediate of formula (9). It has now been found that the intermediates of formula (9) can be readily formed in accordance with the process of this invention with high enantiomeric purity, specific details of which are provided hereinbelow by way of various examples. In general, the enantiomeric purity can be determined by chiral HPLC.

Scheme 2

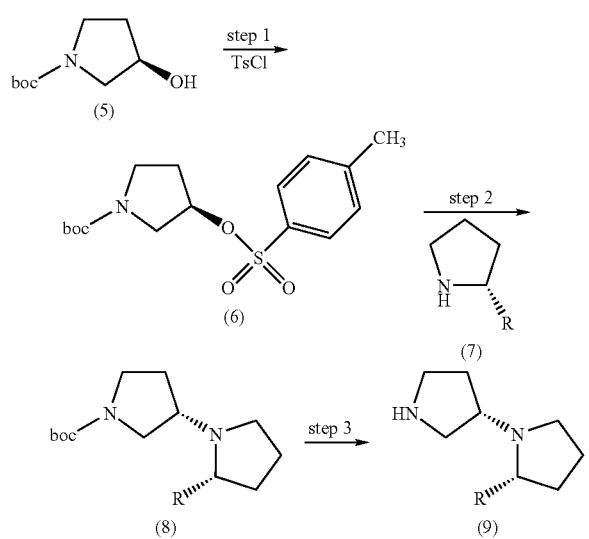

Scheme 3 illustrates the preparation of amino-phenyl-pyrrolidinyl-pyrrolidine intermediate of formula (12), wherein R, $R_1$ and $R_2$ are as defined herein. In step 1, Scheme 3, suitably substituted nitrobenzene of formula (10), wherein X is a suitable leaving group, such as Cl, F, Br, or triflate (OTf) is condensed with the [1,3']pyrrolidinyl-pyrrolidine of formula (4) in order to form an intermediate of formula (11). Such condensation reactions can again be carried out using any of the procedures known to one skilled in the art. For example, such condensation reaction can be carried out in a polar solvent such as DMSO in the presence of a base such as potassium carbonate at ambient to super-ambient temperature conditions.

In step 2, Scheme 3, intermediate of formula (11) is reduced by hydrogenation or other known chemical methods, such as using tin dichloride in hydrochloric acid, to form the key intermediate (12).

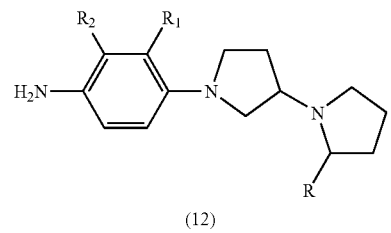

Scheme 4 illustrates the preparation of compounds of formula (I) of this invention using either Method A or Method B depending upon the availability of desired carboxylic acid of formula $R_4$—$CO_2H$ either in the form of acid itself or its acid chloride, wherein R, $R_1$, $R_2$ and $R_4$ are as described herein and $R_3$ is hydrogen.

In Method A, Scheme 4 the acid chloride of formula (13) can be reacted with the intermediate (12) using any of the conditions known to one skilled in the art. Typically, such conditions include without any limitations reaction of the acid chloride with the intermediate of formula (12) in a suitable organic solvent such as for example dichloromethane in the presence of a suitable base such as pyridine. Such reactions are generally carried out at sub-ambient temperature conditions, for example around 0° C., however ambient to super-ambient temperature conditions may also be suitable in certain situations depending upon the nature of the acid chloride and the intermediate (12).

Similarly, in Method B, Scheme 4, the carboxylic acid of formula (14) can be reacted with the intermediate of formula (12) under various reaction conditions known to one skilled in the art. For instance, the acid of formula (14) is reacted with intermediate of formula (12) at sub-ambient temperature conditions in the presence of suitable reagents such as for example a mixture of N-methylmorpholine, 1-hydroxybenzotriazole and EDC.

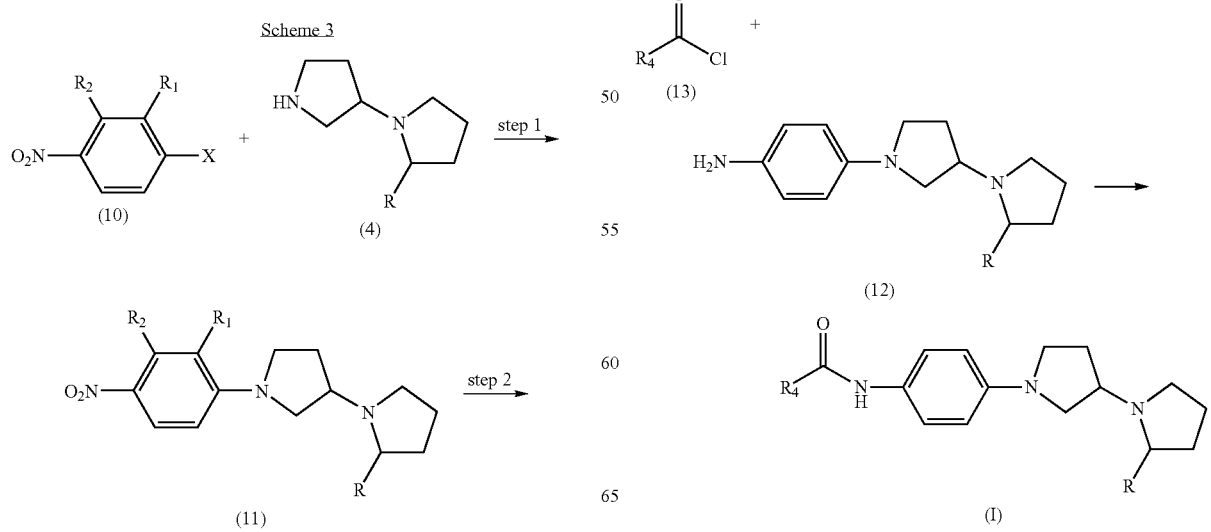

Method B

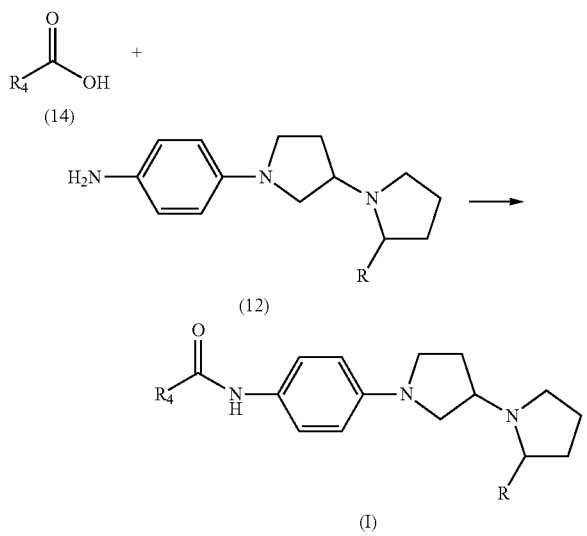

As already noted hereinabove, the compounds of this invention can readily be converted into salts. More particularly, the compounds of the present invention are basic, and as such compounds of this invention are useful in the form of the free base or in the form of a pharmaceutically acceptable acid addition salt thereof. Acid addition salts may be a more convenient form for use; and, in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compound is preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures.

In another aspect of this embodiment, a specific disease, a disorder or a condition that can be treated with the compound of this invention include, without any limitation the following: sleep-related disorders (specific examples include without any limitation narcolepsy, circadian rhythm sleep disorders, obstructive sleep apnea, periodic limb movement and restless leg syndrome, excessive sleepiness and drowsiness due to medication side-effect, etc.), neurological disorders (specific examples that may be enumerated include but not limited to dementia, Alzheimer's disease, multiple sclerosis, epilepsy and neuropathic pain), neuropsychological and cognitive disorders (a few of the specific examples include without any limitation include schizophrenia, attention deficit/hyperactivity disorder, Alzheimer's Disease, depression, seasonal affective disorder, and cognitive impairment).

As described hereinbelow by way of specific examples, the compounds of formula (I) bind to the H3 receptors and demonstrate inverse agonism versus H3 functional activity. Therefore, the compounds of this invention may have utility in the treatment of diseases or conditions ameliorated with H3 receptor ligands. More specifically, the compounds of the present invention are H3 receptor ligands that modulate function of the H3 receptor by antagonizing the activity of the receptor. Further, the compounds of this invention may be inverse agonists that inhibit the basal activity of the receptor or they may be antagonists that completely block the action of receptor-activating agonists. Additionally, the compounds of this invention may also be partial agonists that partially block or partially activate the H3 receptor or they may be agonists that activate the receptor. Thus the compounds of this invention may act differentially as antagonists, inverse agonists and/or partial agonists depending on functional output, histamine tone and or tissue context. Accordingly, the differential activities of these compounds may allow for utility to ameliorate multiple disease states as specifically enumerated above.

Thus in one aspect of this invention there is provided a method of treating a disease in a patient, said disease selected from the group consisting of sleep related disorder, dementia, Alzheimer's disease, multiple sclerosis, cognitive disorder, attention deficit hyperactivity disorder and depression, comprising administering to said patient a therapeutically effective amount of a compound of formula (I).

One of skill in the art readily appreciates that the pathologies and disease states expressly stated herein are not intended to be limiting rather to illustrate the efficacy of the compounds of the present invention. Thus it is to be understood that the compounds of this invention may be used to treat any disease caused by the effects of H3 receptors. That is, as noted above, the compounds of the present invention are modulators of H3 receptors and may be effectively administered to ameliorate any disease state which is mediated all or in part by H3 receptors.

All of the various embodiments of the compounds used in the methods of this invention as disclosed herein can be used in the method of treating various disease states as described herein. As stated herein, the compounds used in the method of this invention are capable of inhibiting the effects of H3 receptor and thereby alleviating the effects and/or conditions caused due to the activity of H3.

In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal or topical route.

Finally, in yet another embodiment of this invention, there is also provided a pharmaceutical composition comprising a pharmaceutically acceptable carrier and a compound of formula (I), including enantiomers, stereoisomers, and tautomers of said compound and pharmaceutically acceptable salts, solvates or derivatives thereof, with said compound having the general structure shown in formula I as described herein.

As described herein, the pharmaceutical compositions of this invention feature H3 inhibitory activity and thus are useful in treating any disease, condition or a disorder caused due to the effects of H3 in a patient. Again, as described above, all of the preferred embodiments of the compounds of this invention as disclosed herein can be used in preparing the pharmaceutical compositions as described herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal or topical route. The preferred administrations of the pharmaceutical composition of this invention are by oral and intranasal routes. Any of the known methods to administer pharmaceutical compositions by an oral or an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

EXAMPLES

General

As used in the examples and preparations that follow, the terms used therein shall have the meanings indicated: "kg" refers to kilograms, "g" refers to grams, "mg" refers to milligrams, "μg" refers to micrograms, "pg" refers to picograms, "lb" refers to pounds, "oz" refers to ounces, "mol" refers to moles, "mmol" refers to millimoles, "gmole" refers to micromoles, "nmole" refers to nanomoles, "L" refers to liters, "mL" or "ml" refers to milliliters, "μL" refers to microliters, "gal" refers to gallons, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "DMSO" refers to dimethyl sulfoxide, "DMF" refers to N,N-dimethylformamide, "CDI" refers to 1,1'-carbonyldiimidazole, "DCM" or "$CH_2Cl_2$" refers to dichloromethane, "DCE" refers to 1,2-dichloroethane, "HCl" refers to hydrochloric acid, "EtOAc" refers to ethyl acetate, "PBS" refers to Phosphate Buffered Saline, "IBMX" refers to 3-isobutyl-1-methylxanthine, "PEG" refers to polyethylene glycol, "MeOH" refers to methanol, "$MeNH_2$" refers to methyl amine, "$N_2$" refers to nitrogen gas, "iPrOH" refers to isopropyl alcohol, "$Et_2O$" refers to ethyl ether, "LAH" refers to lithium aluminum hydride, "heptane" refers to n-heptane, "HMBA-AM" resin refers to 4-hydroxymethylbenzoic acid amino methyl resin, "$PdCl_2(dppf)_2$" refers to 1,1'-bis(diphenylphosphino)ferrocene-palladium (II) dichloride DCM complex, "HBTU" refers to 2-(1H-benzotriazol-1yl)-1,1,3,3-tetramethyluronium hexafluorophosphate, "DIEA" refers to diisopropylethylamine, "CsF" refers to cesium fluoride, "MeI" refers to methyl iodide, "AcN," "MeCN" or "$CH_3CN$" refers to acetonitrile, "TFA" refers to trifluoroacetic acid, "THF" refers to tetrahydrofuran, "DMF" refers to dimethylformamide, "NMP" refers to 1-methyl-2-pyrrolidinone, "$H_2O$" refers to water, "BOC" refers to t-butyloxycarbonyl, "brine" refers to a saturated aqueous sodium chloride solution, "M" refers to molar, "mM" refers to millimolar, "μM" refers to micromolar, "nM" refers to nanomolar, "N" refers to normal, "TLC" refers to thin layer chromatography, "HPLC" refers to high performance liquid chromatography, "HRMS" refers to high resolution mass spectrum, "L.O.D." refers to loss on drying, "μCi" refers to microcuries, "i.p." refers to intraperitoneally, "i.v." refers to intravenously, anhyd=anhydrous; aq=aqueous; min=minute; hr=hour; d=day; sat.=saturated; s=singlet, d=doublet; t=triplet; q=quartet; m=multiplet; dd=doublet of doublets; br=broad; LC=liquid chromatograph; MS=mass spectrograph; ESI/MS=electrospray ionization/mass spectrograph; RT=retention time; M=molecular ion, "~"=approximately.

Reactions generally are run under a nitrogen atmosphere. Solvents are dried over magnesium sulfate and are evaporated under vacuum on a rotary evaporator. TLC analyses are performed with EM Science silica gel 60 F254 plates with visualization by UV irradiation. Flash chromatography is performed using Alltech prepacked silica gel cartridges. The $^1$H NMR spectra are run at 300 MHz on a Gemini 300 or Varian Mercury 300 spectrometer with an ASW 5 min probe, and usually recorded at ambient temperature in a deuterated solvent, such as $D_2O$, DMSO-$D_6$ or $CDCl_3$ unless otherwise noted. Chemical shifts values (δ) are indicated in parts per million (ppm) with reference to tetramethylsilane (TMS) as the internal standard.

High Pressure Liquid Chromatography-Mass Spectrometry (LCMS) experiments to determine retention times ($R_T$) and associated mass ions are performed using one of the following methods:

Mass Spectra (MS) are recorded using a Micromass mass spectrometer. Generally, the method used was positive electro-spray ionization, scanning mass m/z from 100 to 1000. Liquid chromatography was performed on a Hewlett Packard 1100 Series Binary Pump & Degasser; Auxiliary detectors used were: Hewlett Packard 1100 Series UV detector, wavelength=220 nm and Sedere SEDEX 75 Evaporative Light Scattering (ELS) detector temperature=46° C., $N_2$ pressure=4 bar.

LCT: Grad (AcN+0.05% TFA):($H_2O$+0.05% TFA)=5:95 (0 min) to 95:5 (2.5 min) to 95:5 (3 min). Column: YMC Jsphere 33×2 4 μM, 1 ml/min MUX: Column: YMC Jsphere 33×2, 1 ml/min Grad (AcN+0.05% TFA):(H2O+0.05% TFA)=5:95 (0 min) to 95:5 (3.4 min) to 95:5 (4.4 min).

LCT2: YMC Jsphere 33×2 4 μM, (AcN+0.05% TFA):(H2O+0.05% TFA)=5:95 (0 min) to 95:5 (3.4 min) to 95:5 (4.4 min)

QU: YMC Jsphere 33×2 1 ml/min, (AcN+0.08% formic acid):(H2O+0.1% formic acid)=5:95 (0 min) to 95:5 (2.5 min) to 95:5 (3.0 min)

The following examples describe the procedures used for the preparation of various starting materials employed in the preparation of the compounds of this invention.

INTERMEDIATES

Intermediate (i)

2-Methyl-[1,3']bipyrrolidinyl-1'-carboxylic acid tert-butyl ester

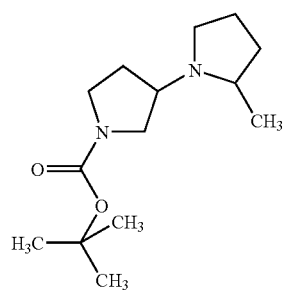

To a solution of N—BOC-3-pyrrolidinone (4.22 g, 22.9 mmol) and 2-methylpyrroline (1.95 g, 22.9 mmol) (HCl salt was made by addition of 22.9 mL of 1 M HCl in ether into the DCM solution of 2-methylpyrroline, then evaporated) in DCE (60 mL) was added powdered sodium triacetoxyborohydride slowly under $N_2$ at r.t. The yellowish milky solution was stirred at r.t. overnight. LC/MS-m/z 255 and 199 (base and M-tBu).

The reaction was quenched with aq. $NaHCO_3$ solution. The two layers were separated, and the aqueous layer was extracted with DCM (20 mL×2). The combined DCM extracts were washed with sodium bicarbonate (10 mL), and brine (5 mL×2), dried (anhydrous potassium carbonate), filtered, and concentrated in vacuo. The crude product was purified on a silica gel column, eluted with DCM and 7.5% MeOH in DCM to get the title compound as a liquid 5.50 g (yield: 94%). MS: 255 (M+H+); TLC: 0.5 (10% MeOH in DCM).

Intermediate (ii)

2-Methyl-[1,3']bipyrrolidinyl hydrochloride

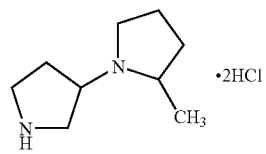

2-Methyl-[1,3']bipyrrolidinyl-1'-carboxylic acid tert-butyl ester (Intermediate (i) obtained above, 5.50 g, 21.62 mmol) was treated with 20 mL of 4 M HCl in dioxane at 0° C. The solution was stirred under nitrogen at r.t. overnight. TLC (10% MeOH in DCM) did not detect the starting material. $N_2$ was passed through the solution with stirring. The outlet was passed though KOH solution to absorb HCl for 30 min. The solvent was removed by evaporation to dryness to get the title compound as a hygroscopic gummy material, 5.3 g (~100%). This material was used without further purification in subsequent steps as illustrated below. LCMS: $R_T$=0.35 minutes, MS: 155 (M+H).

$^1$H NMR ($D_2O$, 300 MHz): 4.30 (m), 3.85 (m), 3.76 (s), 3.5 (m), 3.46 (m), 3.32 (m), 2.66 (m), 2.28 (m), 2.10 (m), 1.46 (bs).

Intermediate (iii)

2-Methyl-1'-(3-methyl-4-nitro-phenyl)-[1,3']bipyrrolidinyl

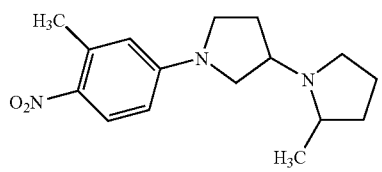

2-Methyl-[1,3']bipyrrolidinyl hydrochloride (Intermediate (ii) obtained above, 5.3 g, 21.6 mmol, 1.12 equiv.) was dissolved in anhydrous DMSO (30 mL). To this solution was added 5-fluoro-2-nitrotoluene (3.00 g, 18.78 mmol, 1 equiv.), followed by powdered potassium carbonate (8.9 g, 65 mmol). The suspension was heated on an oil bath to 85° C. for 4 h when the starting material was consumed as determined by TLC (5% MeOH in DCM) and LC/MS. To the suspension were added 20 mL of water and 50 mL of DCM. The two layers were separated, and the aqueous layer was extracted with DCM (20 mL×2). The combined DCM extracts were washed with sodium bicarbonate (20 mL), and brine (15 mL×2), dried (anhydrous potassium carbonate), filtered, and concentrated in vacuo. The crude product was purified on a silica gel column, eluted with 5% MeOH in DCM to get the title compound as a yellow solid after drying, 5.47 g (100%). MS: 290 (M+H+).

$^1$H NMR (300 MHz, CDCl$_3$), δ (ppm): 8.10 (d, 9 Hz, 1H), 6.36 (bd, 9 Hz, 1H), 6.28 (bs, 1H), 3.4-3.2 (m, 5H), 3.00-2.78 (m, 2H), 2.64 (s, 3H), 1.7-2.2 (m, 6H), 1.5 (m, 1H), 1.06 (m, 3H).

Intermediate (iv)

4-(2-Methyl-[1,3']bipyrrolidinyl-1'-yl)-phenylamine

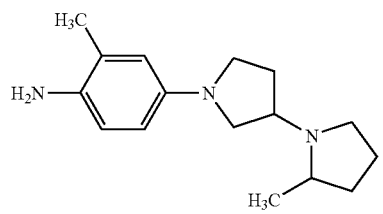

A solution of 2-methyl-1'-(3-methyl-4-nitro-phenyl)-[1,3']bipyrrolidinyl (Intermediate (iii) obtained above, 2.23 g, 7.7 mmol) in MeOH was de-aerated and nitrogen was introduced. To this solution was added Pd—C (10%). This mixture was stirred under H$_2$ atmosphere at r.t. for 8 h. TLC (10% MeOH in DCM) and LC/MS showed the reaction was complete. The mixture was passed through a Celite pad, rinsed with methanol. The filtrate was concentrated to dryness, and further dried under high vacuum to yield a reddish brown liquid after drying under high vacuum to obtain the title compound as a gummy black liquid, 1.73 g (86%). This material was used in the next step without further purification and storage. MS: 260 (M+H$^+$).

Intermediate (v)

2-(2R)-Methyl-[1,3']bipyrrolidinyl hydrochloride

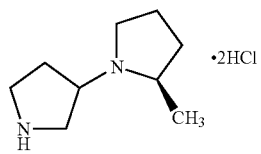

To a solution of N—BOC-3-pyrrolidinone (1.26 g, 6.83 mmol) and 2-(R)-methylpyrroline (0.83 g, 6.83 mmol) in DCE (20 mL) was added powdered sodium triacetoxyborohydride slowly under N$_2$ at r.t. The yellowish milky solution was stirred at r.t. overnight. LC/MS showed m/z 255 and 199 (base peak and M-tBu peak).

The reaction was quenched with aqueous NaHCO$_3$ solution. The two layers were separated, and the aqueous layer was extracted with DCM (10 mL×2). The combined DCM extracts were washed with sodium bicarbonate (10 mL), and brine (5 mL×2), dried (anhydrous potassium carbonate), filtered, and concentrated in vacuo. The crude product was purified on a silica gel column, eluted with DCM and 7.5% MeOH in DCM to get a liquid, 1.29 g (yield: 74%). This thick liquid as obtained above (1.29 g, 5.08 mmol) was treated with 16 mL of 4M HCl in dioxane at 0° C. The solution was stirred under nitrogen at r.t. overnight. TLC (10% MeOH in DCM) did not detect the starting material.

N$_2$ was passed through the solution with stirring. The outlet was passed though KOH solution to absorb HCl for 30 min. The solvent was removed by evaporation to dryness to get a hygroscopic gum (HCl salt and hydrate, exact composition unknown), 1.32 g (~100%). This material was used without further purification in subsequent steps as described below. LCMS: R$_T$=0.35 minutes, MS: 155 (M+H).

Intermediate (vi)

2-(2R)-Methyl-1'-(3-methyl-4-nitro-phenyl)-[1,3']bipyrrolidinyl

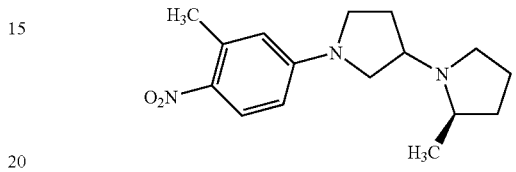

5-Fluoro-2-nitrotoluene (1.55 g, 10 mmol) was dissolved in anhydrous DMSO. To this solution was added 2-(2R)-methyl-[1,3']bipyrrolidinyl hydrochloride (2.30 g, 15 mmol), followed by powdered potassium carbonate. The suspension was heated on an oil bath to 85° C. for 3 h when the starting material was consumed as determined by TLC (5% MeOH/DCM) and LC/MS. To the suspension was added 20 mL of water and 50 mL of DCM. The two layers were separated, and the aqueous layer was extracted with DCM (20 mL×2). The combined DCM extracts were washed with sodium bicarbonate (20 mL), and brine (15 mL×2), dried (anhydrous potassium carbonate), filtered, and concentrated in vacuo. The crude product was purified on a silica gel column, eluted with 5% MeOH in DCM to obtain the title compound as a yellow solid after drying, 2.70 g (93%). MS: 290 (M+1).

$^1$H NMR (CDCl$_3$, 300 MHz), δ (ppm): 8.10 (d, 9 Hz,), 6.36 (bd, 9 Hz), 6.28 (bs) 3.4-3.2 (m), 3.00-2.78 (m), 2.64 (s), 1.7-2.2 (m) 1.5 (m), 1.06 (d, 6.6 Hz), 1.14 (d, 6.6 Hz).

Intermediate (vii)

2-Methyl-4-(2-(2R)-methyl-[1,3']bipyrrolidinyl-1'-yl)-phenylamine

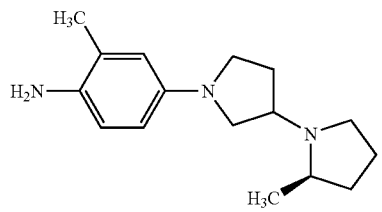

A solution of 2-(2R)-methyl-1'-(3-methyl-4-nitro-phenyl)[1,3']bipyrrolidinyl (2 g, 6.9 mmol) in MeOH (15 mL) was de-aerated and nitrogen was introduced. To this solution was added Pd—C (10%, 0.20 g). The nitrogen was replaced with hydrogen and the mixture was stirred under H$_2$ atmosphere at r.t. overnight. TLC (10% MeOH in DCM) and LC/MS showed the reaction was complete. The mixture was passed through a celite pad, rinsed with methanol. The filtrate was concentrated to dryness, and further dried under high vacuum to yield the title compound as a reddish brown liquid after drying under high vacuum, 2.02 g (100% yield).

Intermediate (viii)

2-(2S)-Methyl-[1,3']bipyrrolidinyl hydrochloride

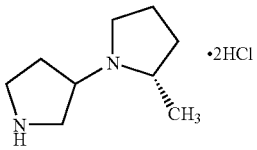

The title compound was prepared in a manner substantially the same as intermediate (v) by condensing N—BOC-3-pyrrolidinone (1.26 g, 6.83 mmol) and 2-(S)-methylpyrroline, followed by de-protection with hydrochloride in dioxane.

LCMS: $R_T$=0.36 minutes, MS: 155 (M+H).

$^1$H NMR (CDCl$_3$, 300 MHz), δ (ppm): 4.16 (m), 3.77 (m), 3.61 (m), 3.13, (m) 3.31 (m), 2.53 (m), 2.41 (m) 1.98 (m), 1.67 (m), 1.31 (m).

Intermediate (ix)

3-(3R)-(Toluene-4-sulfonyloxy)-pyrrolidine-1-carboxylic acid tert-butyl ester

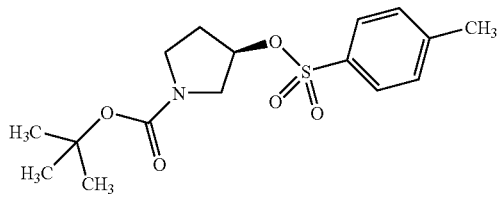

A round-bottomed flask was charged with p-toluenesulfonyl chloride (16.01 g, 83.98 mmol, 1.5 equiv.) and 150 ml of anhydrous DCM. The solution was cooled to an ice-water bath and evacuated and purged with nitrogen. To this solution was added a solution of (3R)-(−)-N—BOC-3-hydroxypyrrolidine (purchased from Aldrich) (10.47 g, 55.99 mmol) in 50 mL of DCM, followed by DMAP (0.66 g) and triethylamine (16.2 mL). The solution was stirred under nitrogen overnight from 0° C. to rt. TLC (5% MeOH in DCM) showed the completion of the reaction. The reaction was quenched by addition of polymer-supported amine (8 g), stirred 30 min. 100 mL of DCM was added. The organic layer was washed with H$_3$PO$_4$ (1M, 2×50 mL), followed by NaHCO$_3$ (50 mL), brine (50 mL), dried (K$_2$CO$_3$), filtered through a silica gel pad, and concentrated to obtain the title compound as a liquid, 15.82 g (82.8%).

MS: 363 (M+Na$^+$); TLC (DCM) R$_f$=0.3.

$^1$H NMR (CDCl$_3$, 300 MHz), δ (ppm): 7.80 (d, 9.0 Hz, 2H), 7.35 (d, 7.8 Hz, 2H), 5.04 (bs, 1H), 3.45 (m, 4H), 2.46 (bs, 3H), 2.05 (m, 2H), 1.43 (s, 9H).

Intermediate (x)

2-(2S)-Methyl-[1,3'(3'S)]bipyrrolidinyl-1'-carboxylic acid tert-butyl ester

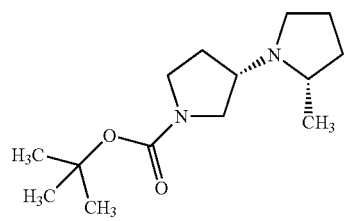

3-(3R)-(Toluene-4-sulfonyloxy)-pyrrolidine-1-carboxylic acid tert-butyl ester (Intermediate (ix) obtained above, 15.82 g, 46.4 mmol, 1 equiv.) and S-(+)-2-methyl-piperindine (obtained from Advanced Asymmetrics), (7.88 g, 92.79 mmol, 2 equiv.) were dissolved in anhydrous CH$_3$CN (150 mL). To this colorless solution was added powdered K$_2$CO$_3$ (powder, 325 mess, 98+%, 14.11 g, 102.08 mmol, 2.2 equiv.) at r.t. The suspension was heated in an oil bath maintained at 80° C. for 24 h. TLC (3% MeOH in DCM for starting material (SM) and 7.5% MeOH in DCM for product) showed that the SM was consumed almost completely. LC/MS showed very little amount of SM at m/z 363, and the product at 255.

The suspension was concentrated to dryness. The residue was taken in water (25 mL) and DCM (80 mL). The two layers were separated, and the aqueous layer was extracted with DCM (20 mL×2). The combined DCM extracts were washed with sodium bicarbonate (25 mL), and brine (25 mL), dried (anhydrous potassium carbonate), filtered, and concentrated in vacuo. The crude product was purified on a silica gel column, eluted with MeOH in DCM (0 to 7.5%) to get the title compound as a gummy material, 7.91 g (67%). LCMS: $R_T$=1.27 minutes, MS: 255 (M+H).

$^1$H NMR (300 MHz, CDCl$_3$), δ (ppm): 3.15 (m, 2H), 3.3 (m, 3H), 2.97 (m, 1H), 2.71 (m, 1H), 2.47 (m, 1H), 1.98 (m, 2H), 1.96-1.67 (m, 4H), 1.46 (s, 9H), 1.06 (d, 6.2 Hz, 3H).

Intermediate (xi)

2-(2R)-Methyl-[1,3'(3'S)]bipyrrolidinyl-1'-carboxylic acid tert-butyl ester

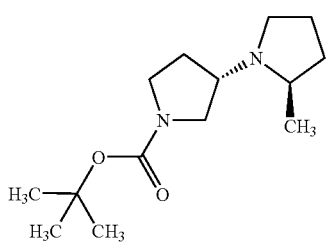

The title compound was prepared in a manner substantially the same as intermediate (x) by condensing 3-(3R)-(toluene-4-sulfonyloxy)-pyrrolidine-1-carboxylic acid tert-butyl ester (Intermediate (ix) obtained above and R-(−)-2-methylpiperindine (obtained from Advanced Asymmetries). LCMS: $R_T$=1.05 minutes, MS: 255 (M+H).

$^1$H NMR (300 MHz, CDCl$_3$), δ (ppm): 3.30 (m, 1H), 3.14 (bs, 2H), 2.91 (m, 1H), 2.75 (m, 1H), 2.51 (m, 1H), 2.07-1.69 (m, 6H), 1.46 (s, 9H), 1.10 (d, 6.0 Hz, 3H).

Intermediate (xii)

3-(3S)-(Toluene-4-sulfonyloxy)-pyrrolidine-1-carboxylic acid tert-butyl ester

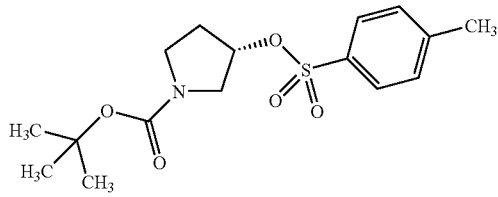

A round bottomed flask was charged with 80 mL of anhydrous DCM. The solvent was evacuated and purged with nitrogen. To this solvent was added (3S)-1-BOC-3-pyrrolidinol (obtained from Astatech), (16.32 g, 33.8 mmol), DMAP (0.4 g). The solution was cooled to an ice-water bath. To this cold solution was added a solution of p-toluene-sulfonyl chloride (9.67 g, 50.87 mmol, 1.5 equiv.) in 20 mL of DCM. The ice-water bath was removed and the solution was stirred under nitrogen overnight. TLC (5% MeOH in DCM for SM, 12 visualization; DCM for product, UV) showed the completion of the reaction. The reaction was quenched by addition of polymer-supported amine (4.5 g), stirred 30 min. 50 mL of DCM was added and filtered. The filtration pad was washed with DCM. The organic was washed with H$_3$PO$_4$ (1M, 2×50 mL), followed by NaHCO$_3$ (50 mL, brine (50 mL), dried (K$_2$CO$_3$), filtered and concentrated to a liquid. This was purified on a 110 g silica gel column on Analogix using 0-2% MeOH in DCM to obtain pure product, 8.82 g (77% yield).

TLC (DCM) Rf=0.3. LC: Rt=3.55 min, 100% pure based on total ion, MS: 363 (M+Na); 342, 327, 286 (base).

$^1$H NMR (300 MHz, CDCl$_3$), δ (ppm): 7.81 (d, 8.7 Hz, 2H), 7.37 (d, 8.7 Hz, 2H), 5.04 (bs, 1H), 3.45 (m, 4H), 2.46 (s, 3H), 1.44 (s, 9H).

Intermediate (xiii)

2-(2S)-Methyl-[1,3'(3'R)]bipyrrolidinyl-1'-carboxylic acid tert-butyl ester

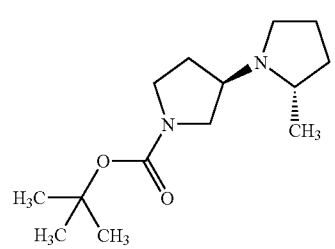

3-(3S)-(Toluene-4-sulfonyloxy)-pyrrolidine-1-carboxylic acid tert-butyl ester (Intermediate (xii) obtained above) (6.82 g, 19.97 mmol, 1 equiv.) and S-(+)-2-methyl-piperindine (obtained from Advanced Asymmetries), (3.40 g, 40 mmol, 2 equiv.) were dissolved in anhydrous CH$_3$CN (65 mL). To this colorless solution was added powder K$_2$CO$_3$ (powder, 325 mess, 98+%, 6.10 g, 44.2 mmol, 2.2 equiv.) at r.t. The suspension was heated with stirring under nitrogen over an oil bath maintained at 80° C. for 24 h. TLC (3% MeOH in DCM for SM, 7.5% MeOH in DCM for product) showed the SM was consumed almost completely. LC/MS showed very little amount of SM at m/z 363.

The suspension was concentrated to dryness. The residue was taken in water (25 mL) and DCM (80 mL). The two layers were separated, and the aqueous layer was extracted with DCM (20 mL×2). The combined DCM extracts were washed with sodium bicarbonate (25 mL), and brine (25 mL), dried (anhydrous potassium carbonate), filtered, and concentrated in vacuo. The crude product was purified on a silica gel column (70 g) on Analogix, eluted with MeOH in DCM (0 to 7.5%) to obtain 4.08 g (80.3%) of the title compound as a gummy material. LCMS: $R_T$=1.14 minutes, MS: 255 (M+H).

$^1$H NMR (300 MHz, CDCl$_3$), δ (ppm): 3.30 (m, 1H), 3.14 (bs, 2H), 2.91 (m, 1H), 2.75 (m, 1H), 2.51 (m, 1H), 2.07-1.69 (m, 6H), 1.46 (s, 9H), 1.10 (d, 6.0 Hz, 3H).

Intermediate (xiv)

2-(2R)-Methyl-[1,3'(3'R)]bipyrrolidinyl-1'-carboxylic acid tert-butyl ester

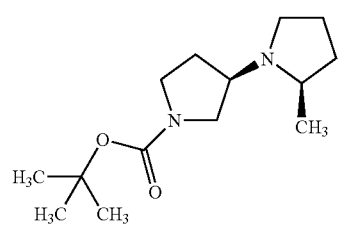

The title compound was prepared in a manner substantially the same as intermediate (xiii) by condensing 3-(3S)-(toluene-4-sulfonyloxy)-pyrrolidine-1-carboxylic acid tert-butyl ester (Intermediate (xiii) obtained above) and R-(−)-2-methylpiperindine (obtained from Advanced Asymmetries). LCMS: $R_T$=1.09 minutes, MS: 255 (M+H).

$^1$H NMR (300 MHz, CDCl$_3$), δ (ppm): 3.15 (m, 2H), 3.3 (m, 3H), 2.97 (m, 1H), 2.71 (m, 1H), 2.47 (m, 1H), 1.98 (m, 2H), 1.96-1.67 (m, 4H), 1.46 (s, 9H), 1.06 (d, 6.2 Hz, 3H).

Intermediate (xv)

Preparation of 2(2S)-methyl-[1,3'(3'R)]bipyrrolidinyl

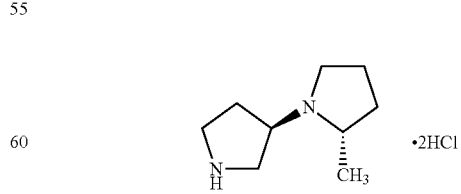

2-(2S)-Methyl-[1,3'(3'R)]bipyrrolidinyl-1'-carboxylic acid tert-butyl ester (7.91 g, 31.14 mmol) was treated with 28.8 mL of HCl in dioxane at 0° C. The solution was stirred under nitrogen at r.t. overnight. Both TLC (10% MeOH in DCM) and LC/MS did not detect the starting material. The reaction was judged complete.

N₂ was passed through the solution with stirring. The outlet was passed through KOH solution to absorb HCl for 1 h. The solvent was removed by evaporation to dryness to get the title compound as a hygroscopic very thick gummy (2HCl salt, hydrated—Exact composition unknown), 8.07 g (~100%). MS: 155 (M+H).

$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H).

Intermediate (xvi)

2(2S)-Methyl-[1,3'(3'S)]bipyrrolidinyl

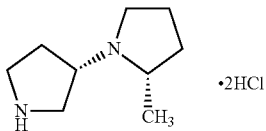

The title compound was prepared in a manner substantially the same as intermediate (xv) by acid hydrolysis of 2-(2S)-methyl-[1,3'(3'S)]bipyrrolidinyl-1'-carboxylic acid tert-butyl ester (Intermediate (x) obtained above).

LCMS: R$_T$=0.37 minutes, MS: 155 (M+H).
$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H)

Intermediate (xvii)

Preparation of 2(2R)-methyl-[1,3'(3'S)]bipyrrolidinyl

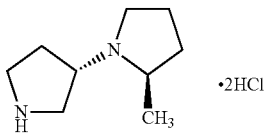

The title compound was prepared in a manner substantially the same as intermediate (xv) by acid hydrolysis of 2-(2R)-methyl-[1,3'(3'S)]bipyrrolidinyl-1'-carboxylic acid tert-butyl ester (Intermediate (xi) obtained above).

Intermediate (xviii)

2(2R)-Methyl-[1,3'(3'R)]bipyrrolidinyl

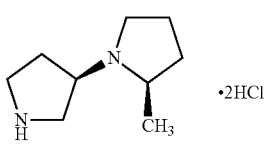

The title compound was prepared in a manner substantially the same as intermediate (xv) by acid hydrolysis of 2-(2R)-methyl-[1,3'(3'R)]bipyrrolidinyl-1'-carboxylic acid tert-butyl ester (Intermediate (xiv) obtained above). MS: 155 (M+H).

$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H)

Intermediate (xix)

2-(2S)-Methyl-1'-(3-methyl-4-nitro-phenyl)-[1,3' (3'R)]bipyrrolidinyl

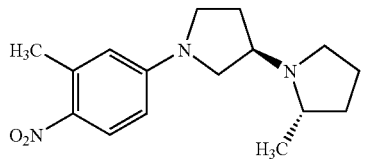

2(2S)-Methyl-[1,3'(3'R)]bipyrrolidinyl (0.23 g, 1.2 mmol) was dissolved in anhydrous DMSO (5 mL) in a flask. To this solution was added 5-fluoro-2-nitrotoluene (223 mg, 1.44 mmol), followed by powdered anhydrous potassium carbonate (662 mg, 4.8 mmol). The suspension was heated on an oil bath to 85° C. for 4 h when the starting material was consumed as shown by TLC (5% MeOH/DCM) and LC/MS. MS: 290 (base peak).

To the suspension were added 2 mL of water and 5 mL of DCM. The two layers were separated, and the aqueous layer was extracted with DCM (10 mL×2). The combined DCM extracts were washed with sodium bicarbonate (5 mL), and brine (5 mL×2), dried (anhydrous potassium carbonate), filtered, and concentrated in vacuo. The crude product was purified on a silica gel column, eluted with 5% MeOH in DCM to get the title compound as a yellow solid after drying.
LCMS: R$_T$=1.38 minutes, MS: 290 (M+H).
$^1$H NMR (300 MHz, CDCl$_3$), δ (ppm): 8.10 (d, 9.1 Hz, 1H), 6.36 (dd, 9.2, 2.5 Hz, 1H), 6.28 (d, 2.4 Hz, 1H), 3.654 (m, 2H), 3.37 (m, 3H), 2.99 (dt, 3.7 Hz, 8.8 Hz, 1H), 2.84 (sixtet, 6.6 Hz, 1H), 2.65 (s, 3H), 2.56 (q, 8.1 Hz, 1H), 2.31 (m, 2H), 2.11 (m, 2H) 1.87 (m, 1H), 1.08 (d, 6.2 Hz, 3H).

The analytical chiral HPLC conditions used were as follows: Isocratic 100% isopropanol with 0.5% IPAmine 5 ml/min outlet pressure 150 bar, 200 nM. The results obtained were as follows: R$_T$=10.92 min; ee 100%

Intermediate (xx)

2-(2S)-Methyl-1'-(3-methyl-4-nitro-phenyl)-[1,3' (3'S]bipyrrolidinyl

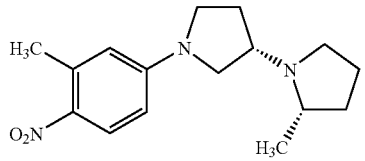

The title compound was prepared in a manner substantially the same as intermediate (xix) by condensing 2(2S)-methyl-[1,3'(3S)]bipyrrolidinyl and 5-fluoro-2-nitrotoluene.
LCMS: R$_T$=1.43 minutes, MS: 290 (M+H).
$^1$H NMR (300 MHz, CDCl$_3$), δ (ppm): 8.10 (d, 9.2 Hz, 1H), 6.36 (dd, 9.2, 2.8 Hz, 1H), 6.28 (d, 2.2 Hz, 1H), 3.6 (m, 2H), 3.3 (m, 3H), 3.00-2.78 (dt, 3.5 Hz, 8.8 Hz, 2H), 2.79 (m, 1H), 2.64 (s, 3H), 2.56 (m, 1H), 2.03 (m, 2H), 1.98 (m, 2H) 1.45 (m, 1H), 1.08 (d, 6.2 Hz, 3H). The analytical chiral HPLC conditions used were as follows: Isocratic 100% isopropanol with 0.5% IPAmine 5 ml/min outlet pressure 150 bar, 200 nM. The results used were as follows:

$R_T$=8.16 min; ee 100%.

Intermediate (xxi)

2-(2R)-Methyl-1'-(3-methyl-4-nitro-phenyl)-[1,3'(3'S)]bipyrrolidinyl

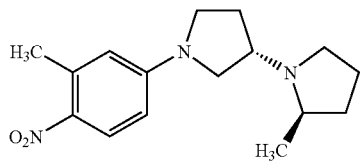

The title compound was prepared in a manner substantially the same as intermediate (xix) by condensing 2(2R)-methyl-[1,3'(3'S)]bipyrrolidinyl and 5-fluoro-2-nitrotoluene.

LCMS: $R_T$=1.41 minutes, MS: 290 (M+H).

$^1$H NMR (300 MHz, CDCl$_3$), δ (ppm): 8.10 (d, 9.1 Hz, 1H), 6.36 (dd, 9.2, 2.5 Hz, 1H), 6.28 (d, 2.4 Hz, 1H), 3.654 (m, 2H), 3.37 (m, 3H), 2.99 (dt, 3.7 Hz, 8.8 Hz, 1H), 2.84 (sixtet, 6.6 Hz, 1H), 2.65 (s, 3H), 2.56 (q, 8.1 Hz, 1H), 2.31 (m, 2H), 2.11 (m, 2H) 1.87 (m, 1H), 1.08 (d, 6.2 Hz, 3H).

The analytical chiral HPLC conditions used were as follows: Isocratic 100% isopropanol with 0.5% IPAmine 5 ml/min outlet pressure 150 bar, 200 nM. The results used were as follows:

$R_T$=11.93 min; ee 100%.

Intermediate (xxii)

2-(2R)-Methyl-1'43-methyl-4-nitro-phenyl)-[1,3'(3'R)]bipyrrolidinyl

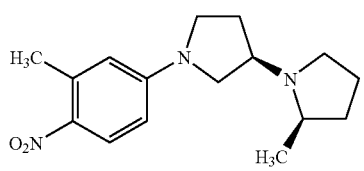

The title compound was prepared in a manner substantially the same as intermediate (xix) by condensing 2(2R)-Methyl-[1,3'(3'R)]bipyrrolidinyl and 5-fluoro-2-nitrotoluene. LCMS: $R_T$=1.43 minutes, MS: 290 (M+H).

$^1$H NMR (300 MHz, CDCl$_3$), δ (ppm): 8.10 (d, 9.2 Hz, 1H), 6.36 (dd, 9.2, 2.8 Hz, 1H), 6.28 (d, 2.2 Hz, 1H), 3.6 (m, 2H), 3.3 (m, 3H), 3.00-2.78 (dt, 3.5 Hz, 8.8 Hz, 2H), 2.79 (m, 1H), 2.64 (s, 3H), 2.56 (m, 1H), 2.03 (m, 2H), 1.98 (m, 2H) 1.45 (m, 1H), 1.08 (d, 6.2 Hz, 3H). The analytical chiral HPLC conditions used were as follows: Isocratic 100% isopropanol with 0.5% IPAmine 5 ml/min outlet pressure 150 bar, 200 nM. The results used were as follows:

$R_T$=8.95 min; ee 100%.

Intermediate (xxiii)

2-Methyl-4-(2-(2S)-methyl-[1,3'(3'R)]bipyrrolidinyl-1'-yl)-phenylamine

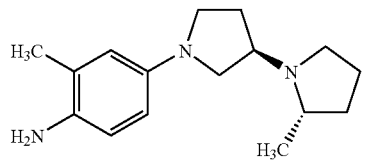

A solution of 2-(2S)-methyl-1'-(3-methyl-4-nitro-phenyl)-[1,3'(3'R)]bipyrrolidinyl (2.02 g, 6.98 mmol) in MeOH (40 mL) was de-aerated and nitrogen was introduced. To this solution was added Pd—C (10%, 0.2 g). This mixture was stirred under H$_2$ atmosphere at r.t. for 4 h. TLC (10% MeOH in DCM) and LC/MS showed the reaction was complete, and the product was detected by MS at 261. The mixture was passed through a Celite pad, rinsed with methanol. The filtrate was concentrated to dryness, and further dried to yield the title compound as a reddish brown liquid after drying under high vacuum, 1.81 g (100%). LC/MS: 260, TLC (10% MeOH/DCM): 0.3 Rf.

Intermediate (xxiv)

2-Methyl-4-(2-(2S)-methyl-[1,3'(3'S)]bipyrrolidinyl-1'-yl)-phenylamine

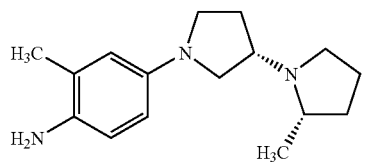

The title compound was prepared in a manner substantially the same as intermediate (xxiii) by hydrogenation of 2-(2S) Methyl-1'-3-methyl-4-nitro-phenyl)-[1,3'(3'S)]bipyrrolidinyl. LC/MS: 260, TLC (10% MeOH/DCM): 0.3 Rf.

Intermediate (xxv)

2-Methyl-4-(2-(2R)-methyl-[1,3'(3'S)]bipyrrolidinyl-1'-yl)-phenylamine

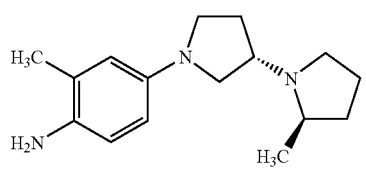

The title compound was prepared in a manner substantially the same as intermediate (xxiii) by hydrogenation of 2-(2R)- methyl-1'-(3-methyl-4-nitro-phenyl)-[1,3'(3'S)]bipyrrolidinyl. LC/MS: 260, TLC (10% MeOH/DCM): 0.3 Rf.

Intermediate (xxvi)

2-Methyl-4-(2(2R)-methyl-[1,3'(3'R)]bipyrrolidinyl-1'-yl)-phenylamine

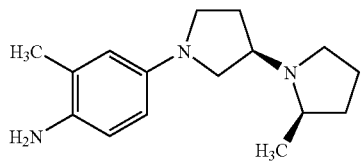

The title compound was prepared in a manner substantially the same as intermediate (xxiii) by hydrogenation of 2-(2R)-Methyl-1'-(3-methyl-4-nitro-phenyl)-[1,3'(3'R)]bipyrrolidinyl. LC/MS: 260, TLC (10% MeOH/DCM): 0.3 Rf.

Example 1

3,5-Dimethyl-isoxazole-4-carboxylic acid [2-methyl-4-(2(2S)-methyl-[1,3'(3'S)]bipyrrolidinyl-1'-yl)-phenyl]-amide

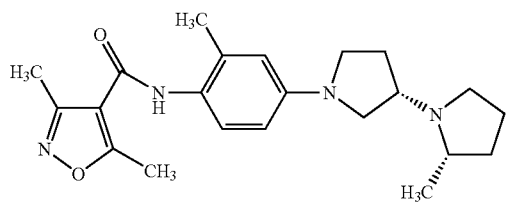

2-Methyl-4-(2(2S)-methyl-[1,3'(3'S)]bipyrrolidinyl-1'-yl)-phenylamine (330 mg, 1.15 mmol) was dissolved in DCM (6 mL) and DMF (2 mL), and the solution was cooled to an ice-water bath. To this solution was added powdered 3,5-dimethyl-isoxazole-4-carboxylic acid (168.9 mg, 1.38 mmol, 1.2 equiv.), N-methylmorpholine (280 mg, 3 equiv.), 1-hydroxybenzotriazole (HOBT) (0.162 g, 1.19 mmol, 1.3 equiv.), sequentially, and finally EDC.HCl (0.228 g, 1.19 mmol, 1.3 equiv.). The resultant clear brown solution was stirred at r.t. overnight. TLC (10% MeOH in DCM) and LC/MS showed that the reaction was complete and the product peak (368) was detected. The reaction was quenched with saturated aqueous sodium bicarbonate solution (3 mL) and 3 mL of DCM. The two layers were separated, and the aqueous layer was extracted with DCM (5 mL×2). The combined DCM extracts were washed with sodium bicarbonate (5 mL), and brine (5 mL), dried (anhydrous potassium carbonate), filtered, and concentrated in vacuo to get a crude product which was purified on a silica gel column (25 g of silica gel) on Analogix to get the title compound as a tan solid, 200 mg (49% yield).

LCMS: $R_T$=1.54 minutes, MS: 383 (M+H).

$^1$H NMR (CDCl$_3$, 300 MHz), δ (ppm): 7.44 (m, 1H), 6.92 (bs, 1H), 6.40 (bs, 1H), 6.39 (bs, 1H), 3.50 (m, 1H), 3.4-3.2 (m, 4H), 3.00 (m, 1H), 2.78 (m, 1H), 2.66 (bs, 3H), 2.48 (bs, 3H), 2.5 (m, 1H), 2.26 (s, 3H), 2.18 (m, 1H), 2.00 (m, 2H), 1.79 (m, 2H), 1.48 (m, 1H), 1.14 (d, 6.3 Hz, 3H).

Example 2

Cyclohexanecarboxylic acid [2-methyl-4-(2S-methyl-[1,3'S]bipyrrolidinyl-1'-yl)-phenyl]-amide trifluoro-acetate

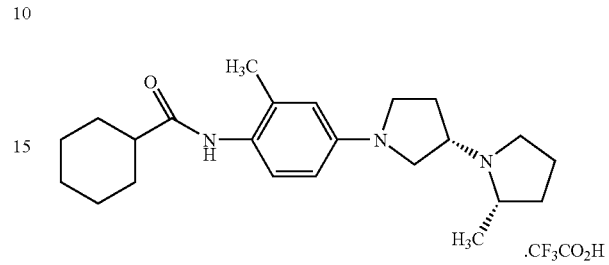

The title compound was prepared in a manner substantially the same as Example 1 by coupling 2-methyl-4-(2(2S)-methyl-[1,3'(3'S)]bipyrrolidinyl-1'-yl)-phenylamine with cyclohexane carboxylic acid. MS: 370.41 (M+H).

Example 3

Bicyclo[2.2.1]heptane-2-carboxylic acid [2-methyl-4-(2S-methyl-[1,3'S]bipyrrolidinyl-1'-yl)-phenyl]-amide trifluoro acetate

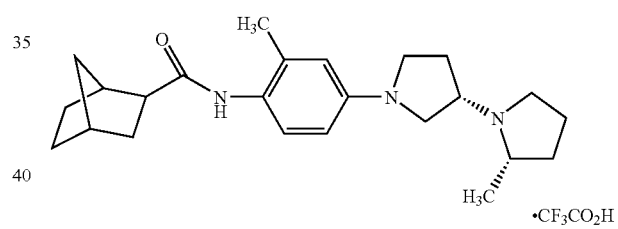

The title compound was prepared in a manner substantially the same as Example 1 by coupling 2-methyl-4-(2(2S)-methyl-[1,3'(3'S)]bipyrrolidinyl-1'-yl)-phenylamine with bicyclo[2.2.1]heptane-2-carboxylic acid. MS: 382.24 (M+H).

Example 4

Tetrahydro-pyran-4-carboxylic acid [2-methyl-4-(2(2S)-methyl-[1,3'(3'S)]bipyrrolidinyl-1'-yl)-phenyl]-amide

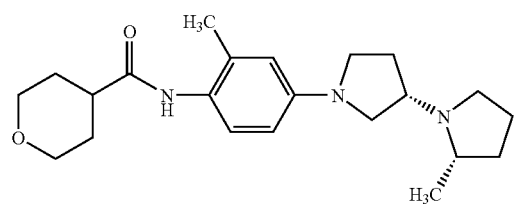

2-Methyl-4-(2(2S)-methyl-[1,3'(3')]bipyrrolidinyl-1'-yl)-phenylamine (330 mg, 1.15 mmol) was dissolved in DCM (6 mL) and DMF (2 mL), and the solution was cooled in an ice-water bath. To this solution was added powdered tetrahydro-pyran-4-carboxylic acid (179.6 mg, 1.38 mmol, 1.2 equiv.), N-methylmorpholine (280 mg, 3 equiv.) and 1-hydroxybenzotriazole (HOBT) (0.162 g, 1.19 mmol, 1.3 equiv.), sequentially, and finally EDC.HCl (0.228 g, 1.19 mmol, 1.3 equiv.). The resultant clear brown solution was stirred at r.t. overnight. TLC (10% MeOH in DCM) and LC/MS showed that the reaction was complete and the product peak (372) was detected. The reaction was quenched with saturated sodium bicarbonate aqueous solution (3 mL) and 3 mL of DCM. The two layers were separated, and the aqueous layer was extracted with DCM (5 mL×2). The combined DCM extracts were washed with sodium bicarbonate (5 mL) and brine (5 mL), dried (anhydrous potassium carbonate), filtered and concentrated in vacuo to obtain a crude product, which was purified on a silica gel column (25 g of silica gel) on Analogix to obtain the title compound as a tan solid, 210 mg (49% yield).

LCMS: $R_T$=1.46 minutes, MS: 372 (M+H).

$^1$H NMR (CDCl$_3$, 300 MHz), δ (ppm): 7.34 (d, 8.2 Hz, 1H), 6.79 (s, 1H), 6.39 (s, 1H), 6.36 (s, 1H), 4.06 (m, 2H), 3.51-3.19 (m, 7H), 3.00 (m, 1H), 2.78 (m, 1H), 2.53 (m, 2H), 2.19 (s, 3H), 2.13-1.73 (m, 10H), 1.47 (m, 1H), 1.14 (d, 6.0 Hz, 3H).

Example 5

3-Methyl-isoxazole-5-carboxylic acid [2-methyl-4-(2S-methyl-[1,3' S]bipyrrolidinyl-1'-yl)-phenyl]-amide trifluoro-acetate

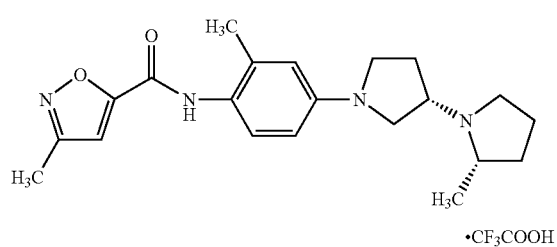

The title compound was prepared in a manner substantially the same as Example 1 by coupling 2-methyl-4-(2(2S)-methyl-[1,3'(3'S)]bipyrrolidinyl-1'-yl)-phenylamine with 3-methyl-isoxazole-5-carboxylic acid. MS: 369.21 (M+H).

Example 6

Furan-3-carboxylic acid [2-methyl-4-(2S-methyl-[1,3'S]bipyrrolidinyl-1'-yl)-phenyl]-amide trifluoro-acetate

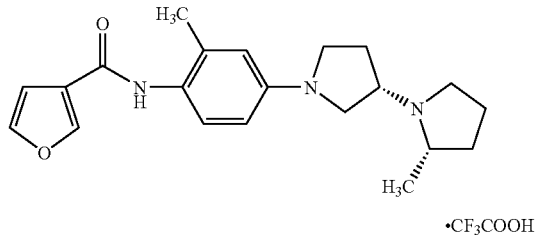

The title compound was prepared in a manner substantially the same as Example 1 by coupling 2-methyl-4-(2(2S)-methyl-[1,3'(3'S)]bipyrrolidinyl-1'-yl)-phenylamine with furan-3-carboxylic acid. MS: 354.21 (M+H).

Example 7

3,5-Dimethyl-isoxazole-4-carboxylic acid [3-methyl-4-(2-methyl-[1,3']bipyrrolidinyl-1'-yl)-phenyl]-amide trifluoro-acetate

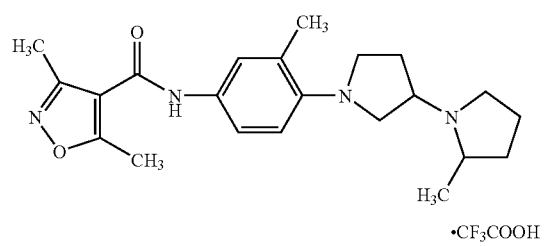

The title compound was prepared in a manner substantially the same as Example 1 by coupling 3-methyl-4-(2-methyl-[1,3']bipyrrolidinyl-1'-yl)-phenylamine with 3,5-dimethyl-isoxazole-4-carboxylic acid. MS: 383.22 (M+H).

Example 8

2-Cyclopentyl-N-[2-methyl-4-(2-methyl-[1,3']bipyrrolidinyl-1'-yl)-phenyl]-acetamide trifluoro-acetate

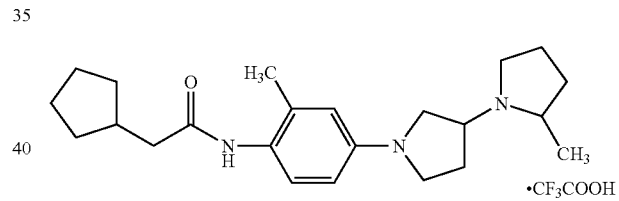

The title compound was prepared in a manner substantially the same as Example 1 by coupling 2-methyl-4-(2-methyl-[1,3']bipyrrolidinyl-1'-yl)-phenylamine with 2-cyclopentyl-acetic acid. MS: 370.23 (M+H).

Example 9

Tetrahydro-pyran-4-carboxylic acid [4-(2-methyl-[1,3']bipyrrolidinyl-1'-yl)-phenyl]-amide trifluoro-acetate

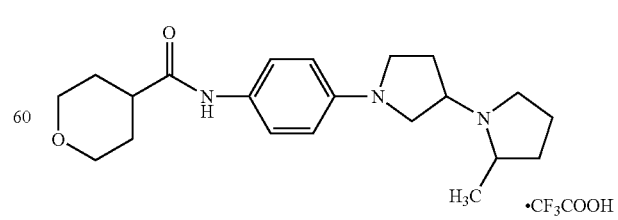

The title compound was prepared in a manner substantially the same as Example 1 by coupling 4-(2-methyl-[1,3']bipyrrolidinyl-1'-yl)-phenylamine with tetrahydro-pyran-4-carboxylic acid. MS: 358.23 (M+H).

Example 10

Cyclopropane carboxylic acid [2-methyl-4-(2-methyl-[1,3']bipyrrolidinyl-1'-yl)-phenyl]-amide trifluoro-acetate

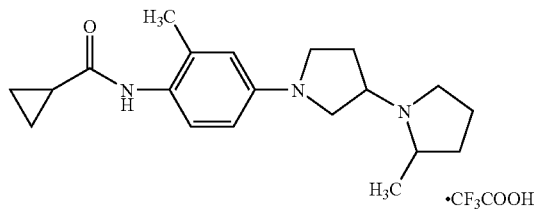

The title compound was prepared in a manner substantially the same as Example 1 by coupling 2-methyl-4-(2-methyl-[1,3']bipyrrolidinyl-1'-yl)-phenylamine with cyclopropanecarboxylic acid. MS: 328.22 (M+H).

Example 11

Tetrahydro-pyran-4-carboxylic acid [3-methyl-4-(2-methyl[1,3']bipyrrolidinyl-1'-yl)-phenyl]-amide trifluoro-acetate

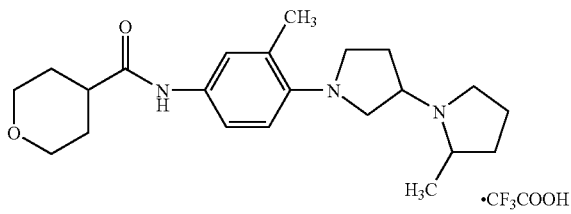

The title compound was prepared in a manner substantially the same as Example 1 by coupling 3-methyl-4-(2-methyl[1,3']bipyrrolidinyl-1'-yl)-phenylamine with tetrahydro-pyran-4-carboxylic acid. MS: 372.27 (M+H).

Example 12

(1S,4R)-Bicyclo[2.2.1]heptane-2-carboxylic acid [2-methyl-4-(2-methyl-[1,3']bipyrrolidinyl-1'-yl)-phenyl]-amide trifluoro-acetate

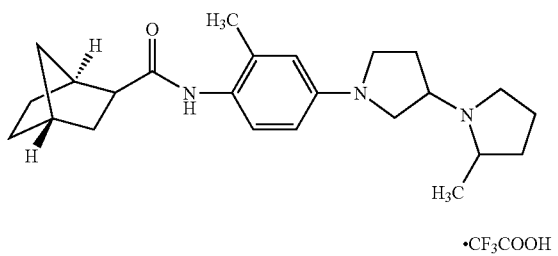

The title compound was prepared in a manner substantially the same as Example 1 by coupling 2-methyl-4-(2-methyl-[1,3']bipyrrolidinyl-1'-yl)-phenylamine with (1S,4R)-bicyclo[2.2.1]heptane-2-carboxylic acid. MS: 382.28 (M+H).

Example 13

1H-Pyrazole-4-carboxylic acid [4-(2-methyl-[1,3']bipyrrolidinyl-1'-yl)-phenyl]-amide trifluoro-acetate

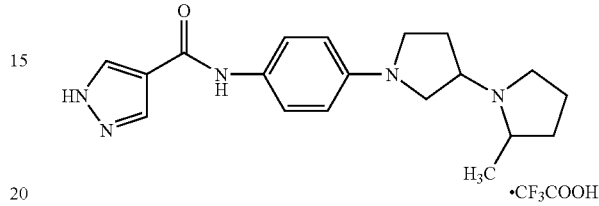

The title compound was prepared in a manner substantially the same as Example 1 by coupling 4-(2-methyl-[1,3']bipyrrolidinyl-1'-yl)-phenylamine with 1H-pyrazole-4-carboxylic acid. MS: 340.22 (M+H).

Example 14

5-Methyl-1H-pyrazole-3-carboxylic acid [2-methyl-4-(2(2S)-methyl-[1,3'(3'S)]bipyrrolidinyl-1'-yl)-phenyl]-amide

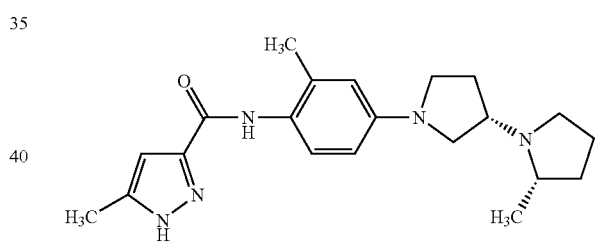

2-Methyl-4-(2(2S)-methyl-[1,3'(3'S)]bipyrrolidinyl-1'-yl)-phenylamine (330 mg, 1.15 mmol) was dissolved in DCM (6 mL) and DMF (2 mL), and the solution was cooled in an ice-water bath. To this solution was added powdered 5-methyl-1H-pyrazole-3-carboxylic acid (174.6 mg, 1.38 mmol, 1.2 equiv.), N-methylmorpholine (280 mg, 3 equiv.), 1-hydroxylbenzotriazole (HOBT) (0.162 g, 1.19 mmol, 1.3 equiv.), sequentially, and finally EDC.HCl (0.228 g, 1.19 mmol, 1.3 equiv.). The resulting clear brown solution was stirred at r.t. overnight. TLC (10% MeOH in DCM) and LC/MS showed that the reaction was complete and the product peak (368) was detected. The reaction was quenched with saturated sodium bicarbonate aqueous solution (3 mL) and 3 mL of DCM. The two layers were separated, and the aqueous layer was extracted with DCM (5 mL×2). The combined DCM extracts were washed with sodium bicarbonate (5 mL) and brine (5 mL), dried (anhydrous potassium carbonate), filtered, and concentrated in vacuo to obtain a crude product which was purified on a silica gel column (25 g of silica gel) on Analogix to obtain the title compound as a tan solid, 207 mg (49% yield).

LCMS: $R_f$=1.61 minutes, MS: 368 (M+H).

$^1$H NMR (300 MHz, CDCl$_3$), δ (ppm): 8.3 ((bs, 1H), 7.65 (d, 9.6 Hz, 1H), 6.64 (s, 1H), 6.43-6.39 (m, 2H), 3.52 (m, 1H), 3.39 (m, 1H), 3.26 (m, 2H), 3.02 (m, 1H), 2.78 (m, 1H), 2.53 (q, 8.1 Hz, 1H), 2.37 (s, 3H), 2.28 (s, 3H), 2.12 (m, 1H), 1.98 (m 2H), 1.78 (m, 2H), 1.51 (m, 2H).

Example 15

1,5-Dimethyl-1H-pyrazole-3-carboxylic acid [2-methyl-4-(2(2S)-methyl-[1,3'(3'S)]bipyrrolidinyl-1'-yl)-phenyl]-amide hydrochloride

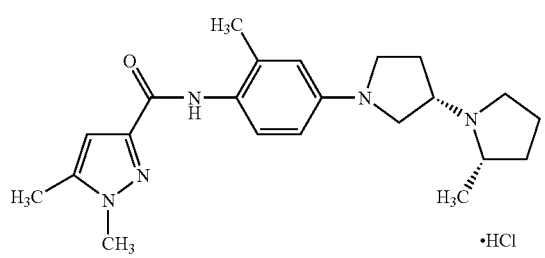

The title compound was prepared in a manner substantially the same as example 16 by coupling 2-methyl-4-(2(2S)-methyl-[1,3'(3'S)]bipyrrolidinyl-1'-yl)-phenylamine with 1,5-dimethyl-1H-pyrazole-3-carboxylic acid. The product obtained was dissolved in DCM and treated with 1N HCl in ether at 0° C. to obtain a hydrochloride salt of the title compound as a tan solid. LCMS: R$_T$=1.76 minutes, MS: 382 (M+H).

$^1$H NMR (DMSO-d6, 300 MHz), δ (ppm): 11.31 (bs), 9.15 (bs), 7.26 (d, 8.7 Hz, 1H), 6.50 (m, 3H), 5.76 (s, 1H), 4.11 (m, 1H), 3.81 (s, 3H) 3.6-3.7 (m, 5H), 3.20 (m, 2H), 2.36 (m, 2H), 2.21 (m, 1H), 2.36 (s, 3H), 2.17 (s, 3H), 1.95 (m, 2H), 1.67 (m, 1H), 1.47 (d, 6.2 Hz, 3H).

Example 16

2,2,3,3-Tetramethyl-cyclopropanecarboxylic acid [2-methyl-4-(2(S)-methyl-[1,3'(S)]bipyrrolidinyl-1'-yl)-phenyl]-amide trifluoroacetate

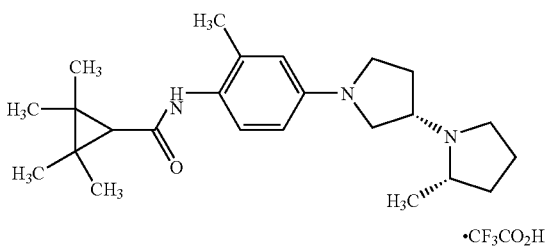

The title compound was prepared in a manner substantially the same as example 1 by coupling 2-methyl-4-(2(S)-methyl-[1,3'(S)]bipyrrolidinyl-1'-yl)-phenylamine with 2,2,3,3-tetramethyl-cyclopropanecarboxylic acid. MS: 384.3 (M+H).

Example 17

2,2,3,3-Tetramethyl-cyclopropanecarboxylic acid [2-methyl-4-(2-methyl-[1,3']bipyrrolidinyl-1'-yl)-phenyl]-amide trifluoroacetate

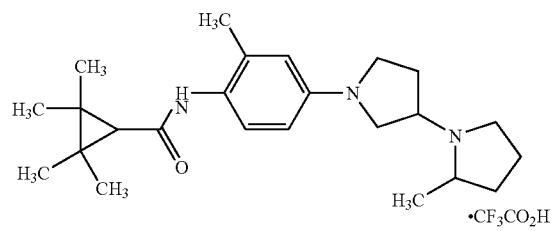

The title compound was prepared in a manner substantially the same as example 1 by coupling 2-methyl-4-(2-methyl-[1,3']bipyrrolidinyl-1'-yl)-phenylamine with 2,2,3,3-tetramethyl-cyclopropanecarboxylic acid. MS: 384.3 (M+H).

Example 18

3,5-Dimethyl-isoxazole-4-carboxylic acid [2-methyl-4-(2-methyl-[1,3']bipyrrolidinyl-1'-yl)-phenyl]-amide trifluoroacetate

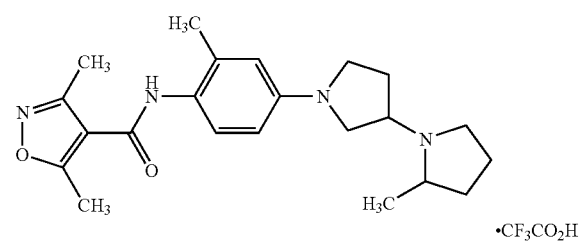

The title compound was prepared in a manner substantially the same as example 1 by coupling 2-methyl-4-(2-methyl-[1,3']bipyrrolidinyl-1'-yl)-phenylamine with 3,5-dimethyl-isoxazole-4-carboxylic acid. MS: 383.3 (M+H).

Example 19

Furan-2-carboxylic acid [2-methyl-4-(2(S)-methyl-[1,3'(S)]bipyrrolidinyl-1'-yl)-phenyl]-amide trifluoroacetate

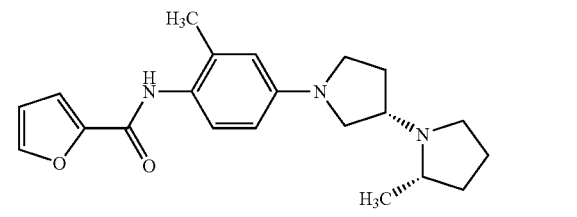

The title compound was prepared in a manner substantially the same as example 1 by coupling 2-methyl-4-(2(S)-methyl-

[1,3'(S)]bipyrrolidinyl-1'-yl)-phenylamine with furan-2-carboxylic acid. MS: 354.3 (M+H).

Example 20

5-Methyl-1H-pyrazole-3-carboxylic acid [2-methyl-4-(2-methyl-[1,3']bipyrrolidinyl-1'-yl)-phenyl]-amide trifluoroacetate

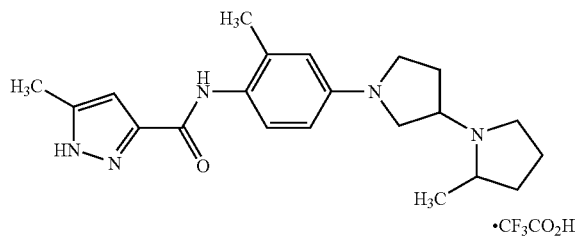

The title compound was prepared in a manner substantially the same as example 1 by coupling 2-methyl-4-(2-methyl-[1,3']bipyrrolidinyl-1'-yl)-phenylamine with 5-methyl-1H-pyrazole-3-carboxylic acid. MS: 368.2 (M+H).

Example 21

2-Cyclopentyl-N-[2-methyl-4-(2(S)-methyl-[1,3'(S)]bipyrrolidinyl-1'-yl)-phenyl]-acetamide trifluoroacetate

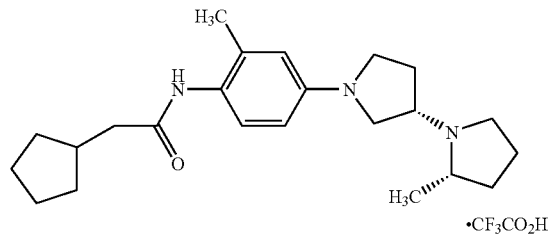

The title compound was prepared in a manner substantially the same as example 1 by coupling 2-methyl-4-(2(S)-methyl-[1,3'(S)]bipyrrolidinyl-1'-yl)-phenylamine with 2-cyclopentyl acetic acid. MS: 370.3 (M+H).

Example 22

5-Methyl-1H-pyrazole-3-carboxylic acid [3-methyl-4-(2-methyl-[1,3']bipyrrolidinyl-1'-yl)-phenyl]-amide trifluoroacetate

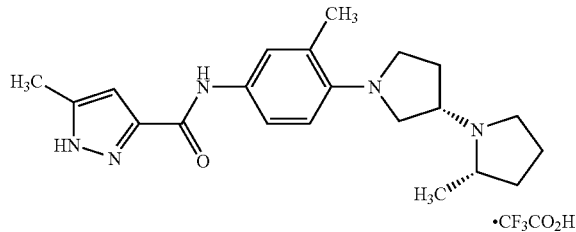

The title compound was prepared in a manner substantially the same as example 1 by coupling 3-methyl-4-(2-methyl-[1,3']bipyrrolidinyl-1'-yl)-phenylamine with 5-methyl-1H-pyrazole-3-carboxylic acid. MS: 368.3 (M+H).

Example 23

(1S,4R)-Bicyclo[2.2.1]heptane-2-carboxylic acid [3-methyl-4-(2-methyl-[1,3']bipyrrolidinyl-1'-yl)-phenyl]-amide trifluoroacetate

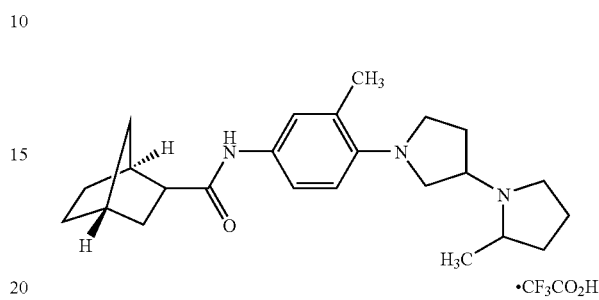

The title compound was prepared in a manner substantially the same as example 1 by coupling 3-methyl-4-(2-methyl-[1,3']bipyrrolidinyl-1'-yl)-phenylamine with (1S,4R)-bicyclo[2.2.1]heptane-2-carboxylic acid. MS: 382.3 (M+H).

Example 24

Tetrahydro-pyran-4-carboxylic acid [2-methyl-4-(2-methyl[1,3']bipyrrolidinyl-1'-yl)-phenyl]-amide trifluoroacetate

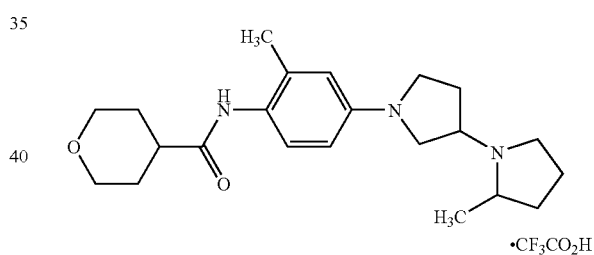

The title compound was prepared in a manner substantially the same as example 1 by coupling 2-methyl-4-(2-methyl-[1,3']bipyrrolidinyl-1'-yl)-phenylamine with tetrahydro-pyran-4-carboxylic acid. MS: 372.3 (M+H).

Example 25

2,2,3,3-Tetramethyl-cyclopropanecarboxylic acid [4-(2-methyl-[1,3']bipyrrolidinyl-1'-yl)-phenyl]-amide trifluoroacetate

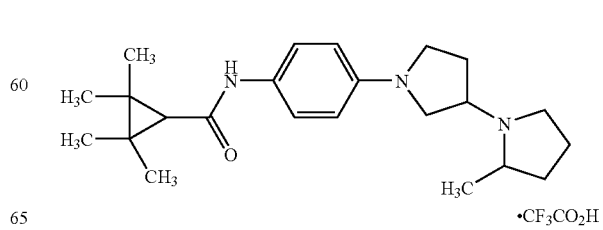

The title compound was prepared in a manner substantially the same as example 1 by coupling 4-(2-methyl-[1,3']bipyrrolidinyl-1'-yl)-phenylamine with 2,2,3,3-tetramethyl-cyclopropanecarboxylic acid. MS: 370.3 (M+H).

Example 26

3,5-Dimethyl-isoxazole-4-carboxylic acid [4-(2-methyl-[1,3']bipyrrolidinyl-1'-yl)-phenyl]-amide trifluoroacetate

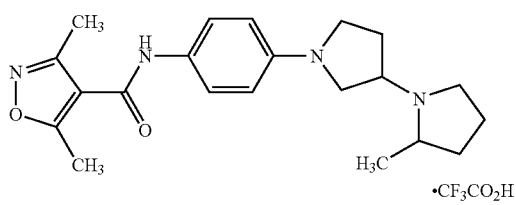

The title compound was prepared in a manner substantially the same as example 1 by coupling 4-(2-methyl-[1,3']bipyrrolidinyl-1'-yl)-phenylamine with 3,5-dimethyl-isoxazole-4-carboxylic acid. MS: 369.2 (M+H).

Example 27

2,2,3,3-Tetramethyl-cyclopropanecarboxylic acid [3-methyl-4-(2-methyl-[1,3']bipyrrolidinyl-1'-yl)-phenyl]-amide trifluoroacetate

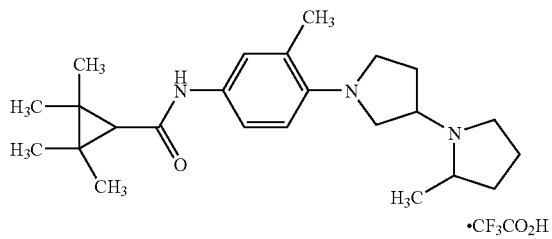

The title compound was prepared in a manner substantially the same as example 1 by coupling 3-methyl-4-(2-methyl-[1,3']bipyrrolidinyl-1'-yl)-phenylamine with 2,2,3,3-tetramethyl-cyclopropanecarboxylic acid. MS: 384.3 (M+H).

Example 28

2-Methyl-oxazole-4-carboxylic acid [2-methyl-4-(2(S)-methyl-[1,3'(S)]bipyrrolidinyl-1'-yl)-phenyl]-amide trifluoroacetate

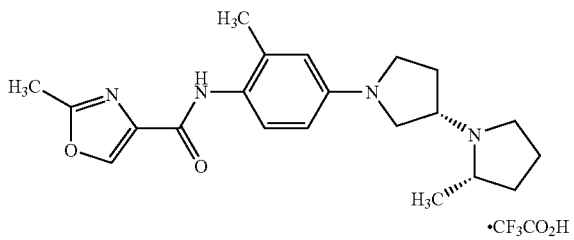

The title compound was prepared in a manner substantially the same as example 1 by coupling 2-methyl-4-(2(S)-methyl-[1,3'(S)]bipyrrolidinyl-1'-yl)-phenylamine with 2-methyl-oxazole-4-carboxylic acid. MS: 369.2 (M+H).

Example 29

(1S,4R)-Bicyclo[2.2.1]heptane-2-carboxylic acid [4-(2-methyl-[1,3']bipyrrolidinyl-1'-yl)-phenyl]-amide trifluoroacetate

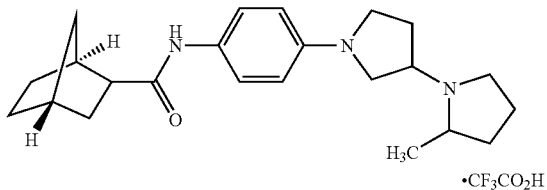

The title compound was prepared in a manner substantially the same as example 1 by coupling 4-(2-methyl-[1,3']bipyrrolidinyl-1'-yl)-phenylamine with (1S,4R)-bicyclo-[2.2.1]heptane-2-carboxylic acid. MS: 368.2 (M+H).

Example 30

Cyclopropanecarboxylic acid [4-(2-methyl-[1,3']bipyrrolidinyl-1'-yl)-2-trifluoromethyl-phenyl]-amide trifluoroacetate

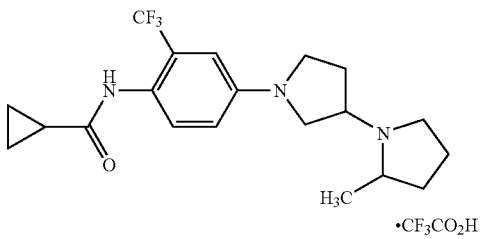

The title compound was prepared in a manner substantially the same as example 1 by coupling 4-(2-methyl-[1,3']bipyrrolidinyl-1'-yl)-2-trifluoromethyl-phenylamine with cyclopropanecarboxylic acid. MS: 382.2 (M+H).

Example 31

5-Methyl-1H-pyrazole-3-carboxylic acid [4-(2-methyl-[1,3']bipyrrolidinyl-1'-yl)-phenyl]-amide trifluoroacetate

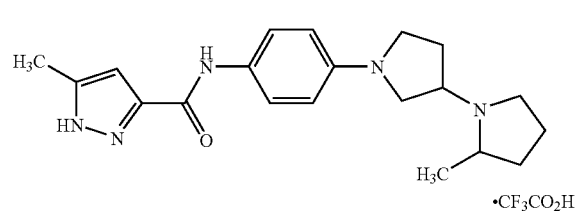

The title compound was prepared in a manner substantially the same as example 1 by coupling 4-(2-methyl-[1,3']bipyrrolidinyl-1'-yl)-phenylamine with 5-methyl-1H-pyrazole-3-carboxylic acid. MS: 354.2 (M+H).

Example 32

5-(2-Oxo-2H-pyridin-1-yl)-furan-2-carboxylic acid [2-methyl-4-(2-methyl-[1,3]bipyrrolidinyl-1'-yl)-phenyl]-amide

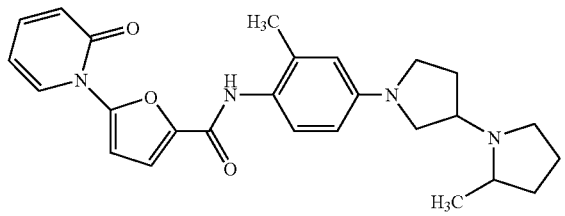

The title compound was prepared in a manner substantially the same as example 1 by coupling 2-methyl-4-(2-methyl-[1,3']bipyrrolidinyl-1'-yl)-phenylamine with 5-(2-oxo-2H-pyridin-1-yl)-furan-2-carboxylic acid. MS: 447.2 (M+H).

Example 33

1H-Pyrazole-4-carboxylic acid [2-methyl-4-(2-methyl-[1,3']bipyrrolidinyl-1'-yl)-phenyl]-amide trifluoroacetate

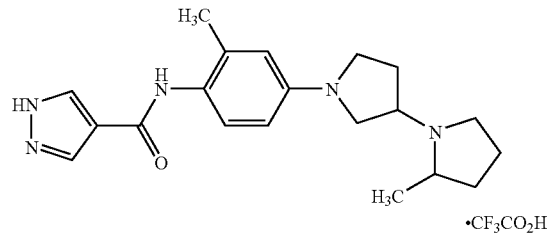

The title compound was prepared in a manner substantially the same as example 1 by coupling 2-methyl-4-(2-methyl-[1,3']bipyrrolidinyl-1'-yl)-phenylamine with 1H-pyrazole-4-carboxylic acid. MS: 354.2 (M+H).

Example 34

1H-Pyrazole-4-carboxylic acid [3-methyl-4-(2-methyl-[1,3']bipyrrolidinyl-1'-yl)-phenyl]-amide trifluoroacetate

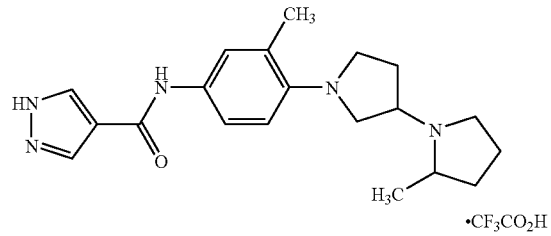

The title compound was prepared in a manner substantially the same as example 1 by coupling 3-methyl-4-(2-methyl-[1, 3']bipyrrolidinyl-1'-yl)-phenylamine with 1H-pyrazole-4-carboxylic acid. MS: 354.3 (M+H).

Example 35

5-Methyl-1H-pyrazole-3-carboxylic acid [4-(2-methyl-[1,3']bipyrrolidinyl-1'-yl)-2-trifluoromethyl-phenyl]-amide trifluoroacetate

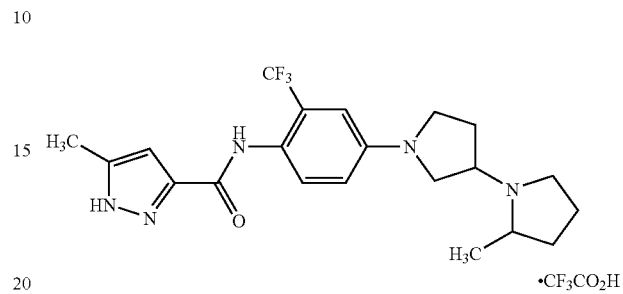

The title compound was prepared in a manner substantially the same as example 1 by coupling 4-(2-methyl-[1,3']bipyrrolidinyl-1'-yl)-2-trifluoromethyl-phenylamine with 5-methyl-1H-pyrazole-3-carboxylic acid. MS: 422.2 (M+H).

Example 36

2-Cyclopentyl-N-[4-(2-methyl-[1,3']bipyrrolidinyl-1'-yl)-phenyl]-acetamide trifluoroacetate

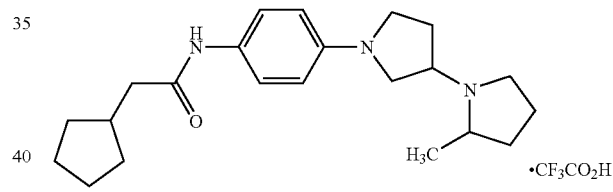

The title compound was prepared in a manner substantially the same as example 1 by coupling 4-(2-methyl-[1,3']bipyrrolidinyl-1'-yl)-phenylamine with cyclopentyl-acetic acid. MS: 356.2 (M+H).

Example 37

5-Pyridin-4-yl-2H-pyrazole-3-carboxylic acid [2-methyl-4-(2-methyl-[1,3']bipyrrolidinyl-1'-yl)-phenyl]-amide trifluoroacetate

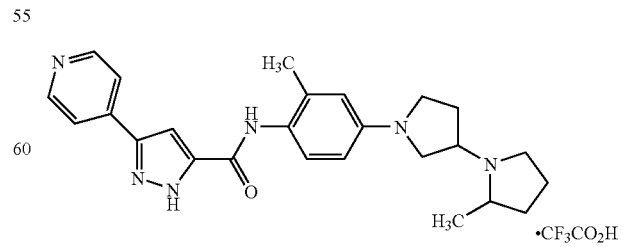

The title compound was prepared in a manner substantially the same as example 1 by coupling 2-methyl-4-(2-methyl-[1, 3']bipyrrolidinyl-1'-yl)-phenylamine with 5-pyridin-4-yl-2H-pyrazole-3-carboxylic acid. MS: 431.3 (M+H).

Example 38

2-Cyclopentyl-N-[3-methyl-4-(2-methyl-[1,3']bipyrrolidinyl-1'-yl)-phenyl]-acetamide trifluoroacetate

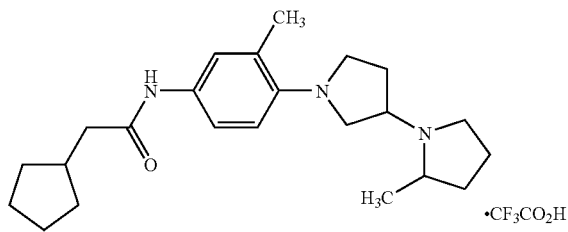

The title compound was prepared in a manner substantially the same as example 1 by coupling 3-methyl-4-(2-methyl[1,3']bipyrrolidinyl-1'-yl)-phenylamine with cyclop entyl-acetic acid. MS: 370.2 (M+H).

Example 39

Cyclopentane carboxylic acid [2-methyl-4-(2(S)-methyl-[1,3' (S)]bipyrrolidinyl-1'-yl)-phenyl]-amide trifluoroacetate

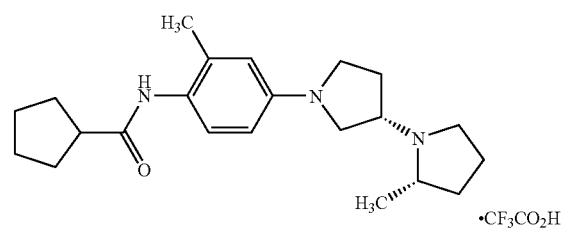

The title compound was prepared in a manner substantially the same as example 1 by coupling 2-methyl-4-(2(S)-methyl-[1,3'(S)]bipyrrolidinyl-1'-yl)-phenylamine with cyclopentanecarboxylic acid. MS: 356.3 (M+H).

Example 40

Cyclopropanecarboxylic acid [4-(2-methyl-[1,3'] bipyrrolidinyl-1'-yl)-phenyl]-amide trifluoroacetate

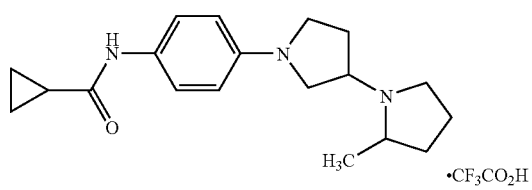

The title compound was prepared in a manner substantially the same as example 1 by coupling 4-(2-methyl-[1,3']bipyrrolidinyl-1'-yl)-phenylamine with cyclopropane-carboxylic acid. MS: 314.2 (M+H).

Example 41

Cyclopropanecarboxylic acid [3-methyl-4-(2-methyl [1,3']bipyrrolidinyl-1'-yl)-phenyl]-amide trifluoroacetate

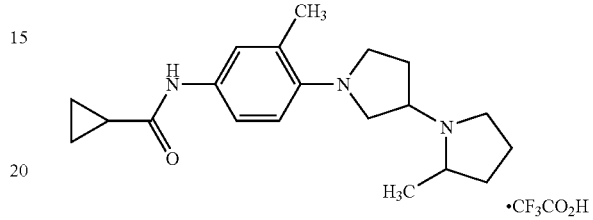

The title compound was prepared in a manner substantially the same as example 1 by coupling 3-methyl-4-(2-methyl[1, 3']bipyrrolidinyl-1'-yl)-phenylamine with cyclopropanecarboxylic acid. MS: 328.2 (M+H).

Biological Examples

Example 42

This Example 42 demonstrates the efficacy of compounds of this invention as H3 receptor ligands. The compounds of this invention have been demonstrated to displace [$^3$H]-Methylhistamine radioligand binding to mammalian cell membranes expressing rhesus (*Macaca Mulatta*) H3 receptor. These compounds display rhesus H3 affinity constants (Ki) in the range of 1 μM to <1 nM. Additionally, the compounds of this invention have been demonstrated by GTPγS radioligand binding assay to inhibit rhesus H3 constitutive functional activity in cell membranes. This inhibition of basal rhesus H3-mediated FTHγS radioligand binding demonstrates that the compounds of this invention find utility as inverse agonists. These compounds decreased rhesus H3 GTPγS radioligand binding by 0-40% below basal levels.

Rhesus H3 membranes were prepared from the Flp-In T-REx 293 Cell Line (Invitrogen) stably transfected with pcDNA5/FRT/TO (Invitrogen) containing the rhesus monkey (*Macaca Mulatta*) 445 amino acid H3 receptor. (Genbank #AY231164). Stably transfected cultures were amplified in tissue culture flasks by standard tissue culture methods and induced to express rhesus H3 by exposure to 500 ng/ml tetracycline (Cellgro) for 24 hours. After induction, cells were dissociated from flasks utilizing Cell Stripper (Cellgro). Cells were centrifuged (1K×g, 5 min) and pellet frozen in an ethanol-dry ice bath to disrupt cell membranes. Frozen cell pellet was re-suspended in 5 mM HEPES (pH 7.4, Invitrogen) at 10 ml/1000 cm2 of harvested cells. The cell suspension was drawn through an 18 gauge needle (2-3×) followed by a 23 gauge needle (2-3×) to further disrupt cell membranes. The cell suspension was centrifuged (40K×g, 30 min). Cell membrane pellet was re-suspended in 5 mM HEPES (pH 7.4, Invitrogen) at a final protein concentration of 10 mg/ml. Rhesus H3 membranes were stored under liquid nitrogen prior to use in [3H]-Methylhistamine and GTPγS radioligand binding assays.

Rhesus H3 radioligand binding assay was performed using rhesus H3 receptor membranes (prepared as described above), [3H]-Methylhistamine (Perkin Elmer) and WGA SPA beads (wheat germ agglutinin scintillation proximity assay) beads (Amersham). The assay was performed in 96-well Opti-Plates (Packard). Each reaction contained 50 µl rhesus H3 membranes (20-30 µg total protein), 50 µl WGA SPA beads (0.1 µg) and 50 µl of 83 Ci/mmol [$^3$H]-Methylhistamine (final concentration 2 nM) and 50 µl of tested compound. The compounds of this invention and/or vehicle were diluted with binding buffer from 10 mM DMSO stocks. Assay plates were sealed with TopSeal (Perkin Elmer) and mixed on shaker (25° C., 1 hour). Assay plates were read on TopCount scintillation counter (Packard). Results were analyzed by Hill transformation and Ki values were determined by Cheng-Prusoff equation. The observed binding data for a few of the representative compounds of this invention are summarized in Table 1.

TABLE 1

| Example No. | Rhesus H3 binding ki (nM) | Inverse Agonism: % inhibition of Basal GTPγS binding in Rhesus H3 |
|---|---|---|
| 6 | 1.8 | −17 |
| 36 | 3.14 | −33 |

Example 43

This Example illustrates selective affinity of the compounds of this invention at H3 receptors and exhibit either low and/or no activity at the MCH receptor site.

The H3 affinity of the compounds of this invention were measured in accordance with the procedures set forth in Example 42 and are summarized in Table 2.

The activity of the compounds of this invention at the MCH receptor site, if any was measured by the procedures as set forth below.

Test Compounds The compounds of this invention were stored in a 96-well microtiter plates (1 µL, 10 mM, 100% DMSO). Each of the test sample was diluted with 249 µL of 100% DMSO (dilution 1:250). The test compounds were further diluted 1:4 (0.1% DMSO) during assay resulting in the final concentration of test compounds of this invention to be 10 µM.

Negative Control: 40 µM of MCH in assay buffer with 0.4% DMSO were transferred to the dilution microtiter plates for control which resulted in final concentration of 10 µM.

Blank: Assay buffer containing 0.4% DMSO were transferred to the dilution microtiter plates for blanks Assay Procedure: The filter plates with 250 mL of 0.5% PEI-solution/well were incubated for 2 hours at room temperature. PEI was removed by vacuum filtration just before pipetting (Univac Polyfiltronic/Whatman). The solution of the compound as prepared above (50 µL), or MCH (negative control) or Puffer/DMSO (positive control) were added to 96-well round bottom microtiter plate. Then 50 µl of [$^{125}$J]-ligand solution was added followed by 100 µl of membrane suspension. The plates were closed with the lids, and incubated for 60 min. at 25° C. The samples were transferred to GF/B filter plate. The reaction mixture was removed by vacuum filtration, washed 4× with 300 µL ice-cold washing buffer and the washing solution was removed by vacuum filtration. The rubber layer at the bottom of the plate was then removed and the filters were dried over night at room temperature. 25 µL of scintillation cocktail was added and the plates were sealed and, plate frames were added and incubated for 1 hour at room temperature. The radioactivity was then measured, settings $^{125}$J standard, 30 sec./well. From this the percent inhibition of ligand binding was measured and tabulated in Table 2.

TABLE 2

| Example No. | Rhesus H3 binding ki (nM) | MCH % inhibition @ 10 µM |
|---|---|---|
| 1 | 0.4 | 0.7 |
| 2 | 0.4 | −2.1 |
| 3 | 0.6 | −0.8 |
| 4 | 1.0 | −1.6 |
| 5 | 1.1 | 3.1 |
| 6 | 1.8 | −6.9 |
| 7 | 3.2 | 5.0 |
| 8 | 8.4 | 1.4 |
| 9 | 8.7 | −2.8 |
| 10 | 9.6 | 4.0 |
| 11 | 17.0 | 2.7 |
| 12 | 19.9 | −2.8 |
| 13 | 22.1 | 4.8 |
| 14 | 4.7 | 28.3 |
| 15 | 10.8 | 10.3 |
| 16 | 0.8 | 5.8 |
| 17 | 37.3 | 11.5 |
| 18 | 2.6 | −2.0 |
| 19 | 3.9 | 6.0 |
| 20 | 30.9 | 24.3 |
| 21 | 0.9 | 1.9 |
| 22 | 17.3 | 5.6 |
| 23 | 130.3 | 11.2 |
| 24 | 6.8 | 8.6 |
| 25 | 143.8 | 15.0 |
| 26 | 2.1 | 9.4 |
| 27 | 65.5 | 36.0 |
| 28 | 4.6 | 7.0 |
| 29 | 15.7 | 11.4 |
| 30 | 14.7 | 1.2 |
| 31 | 44.5 | 30.5 |
| 32 | 33.3 | 10.9 |
| 33 | 24.7 | 9.7 |
| 34 | 125.6 | 16.8 |
| 35 | 307.0 | 23.5 |
| 36 | 3.1 | 0.7 |
| 37 | 14.2 | 34.4 |
| 38 | 10.7 | 3.7 |
| 39 | 0.5 | −7.2 |
| 40 | 9.7 | −3.4 |
| 41 | 17.7 | −1.3 |

Example 44

This Example illustrates the study of efficacy of the compounds of this invention in improving the sleep quality in animal models.

Male Sprague Dawley rats (Charles River, France) weighing 250±10 g were anaesthetized with Zoletil® 50 (60 mg/kg ip) and mounted in a stereotaxic apparatus. Cortical electrodes (small stainless steel screw electrodes of 0.9 mm in diameter) were screwed into the bone over the sensorimotor cortex (1.5 mm lateral to the median suture and 1.5 mm behind the fronto-parietal suture), the visual cortex (1.5 mm lateral to the median suture and 1.5 mm in front of the parieto-occipital suture) and over the cerebellum (reference electrode). Cortical electrodes were attached to a connector (Winchester, 7-lead) and fixed with dental cement to the cranium.

After three weeks of post-operative recovery, animals were placed in plexiglass cylinders (60 cm diameter) with free access to food and water. The temperature of the room was kept constant (21±1° C.) and lights were on from 7 a.m. to 7 p.m. The rats were recorded from 10 a.m. to 4 p.m. during three consecutive days: control day (D1), drug day (D2) and post drug day (D3). Vehicle (D1 and D3) or drug (D2) were administered 15 min before the recording.

Activity in sensorimotor and visual cortices were recorded by comparison with the reference electrode placed over the cerebellar cortex. Three stages were differentiated:
wakefulness (W) characterized by low voltage fast electrocortical (ECoG) activity;
NREM sleep (non rapid eye movement or slow wave sleep: SWS) characterized by an increase in electrocortical activity; development of high-amplitude slow waves with some bursts of sleep spindles;
REM sleep (rapid eye movement or paradoxical sleep: PS) characterized by hypersynchronization of the theta rhythm in the visual area.

Analysis of the ECoG signal was performed automatically by means of a computerized system discriminating between the various sleep phases using sequential spectral analysis of ten seconds periods (Deltamed's software "Coherence").

The compounds of this invention were dissolved in 0.6% MTC tween and administered by oral route (po). The volume of injection was 0.5 ml/100 g of body weight.

Two types of analysis were used to quantify the effects of the compounds of this invention on sleep-wakefulness variables: the one hour-period and the six hour-period analysis.

The results are expressed in minutes (one hour-period analysis) or as the percentage of the control values (100%). Statistical analysis of the data was carried out using the Student's t test for paired values to determine significant variations from control values.

Example 45

Stress-Induced Ultrasonic Vocalizations Test in Adult Rats

This Example illustrates the study of efficacy of the compounds of this invention as antidepressive agents in animal models.

The procedure used was adapted from the technique described by Van Der Poel A. M, Noach E. J. K, Miczek K. A (1989) Temporal patterning of ultrasonic distress calls in the adult rat: effects of morphine and benzodiazepines. *Psychopharmacology* 97:147-8. Rats were placed for a training session in a cage with a stainless steel grid floor (MED Associates, Inc., St. Albans, Vt.). Four electric shocks (0.8 mA, 3s) were delivered every 7s and ultrasonic vocalizations (UV, 22 KHz) were subsequently recorded with the Ultravox system (Noldus, Wageningen, The Netherlands) during 2 min. A modified ultrasound detector (Mini-3 bat model) connected to a microphone was used to transform ultrasonic sound into audible sound. The signal was then filtered and sent to a computer where the Ultravox software recorded each bout of UV that lasted more than 10 ms. Rats were selected on the basis of their UV duration (>40s) and subjected to the test, 4 h after training For the test, rats were placed in the same cage as that used for training. One electric shock (0.8 mA, 3s) was delivered and UV (duration and frequency) were subsequently recorded with the Ultravox system during 2 min. The compounds of this invention were administered p.o. 60 min before testing.

Example 46

Forced-Swimming Test in Rats

This Example further illustrates the study of efficacy of the compounds of this invention as antidepressant agents in animal models.

The procedure was a modification of that described by Porsolt et al. (1977) Depression: a new animal model sensitive to antidepressant treatments. *Nature* 266:730-2. Rats were placed in individual glass cylinder (40 cm height, 17 cm diameter) containing water (21° C.) to a height of 30 cm. Two swimming sessions were conducted (a 15-min training session followed 24 h later by a 6-min test). After each swimming session, rats were placed under a heating lamp to avoid hypothermia. The duration of immobility was measured during the 6-min test. The compounds of this invention were administered p.o. twice (15 min after training session and 60 min before the test).

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:
1. A compound of formula (I):

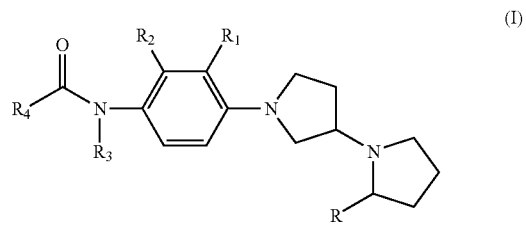

wherein
R, $R_1$, $R_2$ and $R_3$ are the same or different and independently of each other chosen from hydrogen, ($C_1$-$C_4$) alkyl or $CF_3$;
$R_4$ is selected from the group consisting of cyclopropyl, cyclopentyl, cyclohexyl, bicyclo[2,2,1]heptyl, cyclopentylmethyl, tetrahydropyranyl, furanyl, oxazolyl, isoxazolyl and pyrazolyl; wherein said $R_4$ is optionally substituted one or more times with a substituent selected from halogen, methyl, ethyl, pyridinyl, 2-oxo-2H-pyridin-1-yl and $CF_3$; or
a pharmaceutically acceptable salt thereof or an enantiomer or a diastereomer thereof.
2. The compound according to claim 1, wherein R is methyl; $R_2$ is methyl or $CF_3$; $R_1$ and $R_3$ are hydrogen.
3. The compound according to claim 1, wherein R and $R_1$ are methyl; $R_2$ and $R_3$ are hydrogen.
4. The compound according to claim 1, wherein $R_4$ is selected from cyclopropyl, cyclopentyl, cyclohexyl or bicyclo[2.2.1]heptane, which are optionally substituted one or more times with methyl.
5. The compound according to claim 1, wherein $R_4$ is tetrahydropyranyl.
6. The compound according to claim 1, wherein $R_4$ is selected from furanyl, oxazolyl, isoxazolyl and pyrazolyl, which are optionally substituted one or more times with methyl.
7. The compound according to claim 1, wherein $R_4$ is selected from isoxazolyl or isoxazolyl substituted one or more times with methyl.
8. The compound of claim 1 selected from the group consisting of:
cyclopropanecarboxylic acid [2-methyl-4-(2-methyl-[1,3']bipyrrolidinyl-1'-yl)-phenyl]-amide;

cyclopropanecarboxylic acid [4-(2-methyl-[1,3']bipyrrolidinyl-1'-yl)-2-trifluoromethyl-phenyl]-amide;
cyclopropanecarboxylic acid [4-(2-methyl-[1,3']bipyrrolidinyl-1'-yl)-phenyl]-amide;
cyclopropanecarboxylic acid [3-methyl-4-(2-methyl-[1,3']bipyrrolidinyl-1'-yl)-phenyl]-amide;
2,2,3,3-tetramethyl-cyclopropanecarboxylic acid [2-methyl-4-(2(S)-methyl-[1,3'(S)]bipyrrolidinyl-1'-yl)-phenyl]-amide;
2,2,3,3-tetramethyl-cyclopropanecarboxylic acid [2-methyl-4-(2-methyl-[1,3']bipyrrolidinyl-1'-yl)-phenyl]-amide;
2,2,3,3-tetramethyl-cyclopropanecarboxylic acid [4-(2-methyl-[1,3']bipyrrolidinyl-1'-yl)-phenyl]-amide;
2,2,3,3-tetramethyl-cyclopropanecarboxylic acid [3-methyl-4-(2-methyl-[1,3']bipyrrolidinyl-1'-yl)-phenyl]-amide;
cyclopentanecarboxylic acid [2-methyl-4-(2(S)-methyl-[1,3'(S)]bipyrrolidinyl-1'-yl)-phenyl]-amide;
cyclohexanecarboxylic acid [2-methy 1-4-(2S-methyl-[1,3'S]bipyrrolidinyl-1'-yl)-phenyl]-amide;
2-cyclopentyl-N-[2-methyl-4-(2-methyl-[1,3']bipyrrolidinyl-1'-yl)-phenyl]-acetamide;
2-cyclopentyl-N-[2-methyl-4-(2(S)-methyl-[1,3'(S)]bipyrrolidinyl-1'-yl)-phenyl]-acetamide;
2-cyclopentyl-N-[4-(2-methyl-[1,3']bipyrrolidinyl-1'-yl)-phenyl]-acetamide;
2-cyclopentyl-N-[3-methyl-4-(2-methyl-[1,3']bipyrrolidinyl-1'-yl)-phenyl]-acetamide;
bicyclo[2.2.1]heptane-2-carboxylic acid [2-methyl-4-(2S-methyl-[1,3'S]bipyrrolidinyl-1'-yl)-phenyl]-amide;
(1S,4R)-bicyclo[2.2.1]heptane-2-carboxylic acid [2-methyl-4-(2-methyl-[1,3']bipyrrolidinyl-1'-yl)-phenyl]-amide;
(1S,4R)-bicyclo[2.2.1]heptane-2-carboxylic acid [3-methyl-4-(2-methyl-[1,3']bipyrrolidinyl-1'-yl)-phenyl]-amide;
(1S,4R)-bicyclo[2.2.1]heptane-2-carboxylic acid [4-(2-methyl-[1,3']bipyrrolidinyl-1'-yl)-phenyl]-amide;
tetrahydro-pyran-4-carboxylic acid [2-methyl-4-(2(2S)-methyl-[1,3'(3'S)]bipyrrolidinyl-1'-yl)-phenyl]-amide;
tetrahydro-pyran-4-carboxylic acid [4-(2-methyl-[1,3']bipyrrolidinyl-1'-yl)-phenyl]-amide;
tetrahydro-pyran-4-carboxylic acid [3-methyl-4-(2-methyl-[1,3']bipyrrolidinyl-1'-yl)-phenyl]-amide;
tetrahydro-pyran-4-carboxylic acid [2-methyl-4-(2-methyl-[1,3']bipyrrolidinyl-1'-yl)-phenyl]-amide;
furan-3-carboxylic acid [2-methyl-4-(2S-methyl-[1,3'S]bipyrrolidinyl-1'-yl)-phenyl]-amide;
furan-2-carboxylic acid [2-methyl-4-(2(S)-methyl-[1,3'(S)]bipyrrolidinyl-1'-yl)-phenyl]-amide;
5-(2-oxo-2H-pyridin-1-yl)-furan-2-carboxylic acid [2-methyl-4-(2-methyl-[1,3']bipyrrolidinyl-1'-yl)-phenyl]-amide;
2-methyl-oxazole-4-carboxylic acid [2-methyl-4-(2(S)-methyl-[1,3'(S)]bipyrrolidinyl-1'-yl)-phenyl]-amide;
3-methyl-isoxazole-5-carboxylic acid [2-methyl-4-(2S-methyl-[1,3'S]bipyrrolidinyl-1'-yl)-phenyl]-amide;
3,5-dimethyl-isoxazole-4-carboxylic acid [2-methyl-4-(2(2S)-methyl-[1,3'(3'S)]bipyrrolidinyl-1'-yl)-phenyl]-amide;
3,5-dimethyl-isoxazole-4-carboxylic acid [3-methyl-4-(2-methyl-[1,3']bipyrrolidinyl-1'-yl)-phenyl]-amide;
3,5-dimethyl-isoxazole-4-carboxylic acid [2-methyl-4-(2-methyl-[1,3']bipyrrolidinyl-1'-yl)-phenyl]-amide;
3,5-dimethyl-isoxazole-4-carboxylic acid [4-(2-methyl-[1,3']bipyrrolidinyl-1'-yl)-phenyl]-amide;
1H-pyrazole-4-carboxylic acid [4-(2-methyl-[1,3']bipyrrolidinyl-1'-yl)-phenyl]-amide;
1H-pyrazole-4-carboxylic acid [2-methyl-4-(2-methyl-[1,3']bipyrrolidinyl-1'-yl)-phenyl]-amide;
1H-pyrazole-4-carboxylic acid [3-methyl-4-(2-methyl-[1,3']bipyrrolidinyl-1'-yl)-phenyl]-amide;
5-methyl-1H-pyrazole-3-carboxylic acid [2-methyl-4-(2(2S)-methyl-[1,3'(3'S)]bipyrrolidinyl-1'-yl)-phenyl]-amide;
5-methyl-1H-pyrazole-3-carboxylic acid [2-methyl-4-(2-methyl-[1,3']bipyrrolidinyl-1'-yl)-phenyl]-amide;
5-methyl-1H-pyrazole-3-carboxylic acid [3-methyl-4-(2-methyl-[1,3']bipyrrolidinyl-1'-yl)-phenyl]-amide;
5-methyl-1H-pyrazole-3-carboxylic acid [4-(2-methyl-[1,3']bipyrrolidinyl-1'-yl)-phenyl]-amide;
5-methyl-1H-pyrazole-3-carboxylic acid [4-(2-methyl-[1,3']bipyrrolidinyl-1'-yl)-2-trifluoromethyl-phenyl]-amide;
1,5-dimethyl-1H-pyrazole-3-carboxylic acid [2-methyl-4-(2(2S)-methyl-[1,3'(3'S)]bipyrrolidinyl-1'-yl)-phenyl]-amide; and
5-pyridin-4-yl-2H-pyrazole-3-carboxylic acid [2-methyl-4-(2-methyl-[1,3']bipyrrolidinyl-1'-yl)-phenyl]-amide;
or a pharmaceutically acceptable salt thereof.

9. The compound of claim 1 selected from the group consisting of:
cyclopropanecarboxylic acid [2-methyl-4-(2-methyl-[1,3']bipyrrolidinyl-1'-yl)-phenyl]-amide;
2-cyclopentyl-N-[2-methyl-4-(2-methyl-[1,3']bipyrrolidinyl-1'-yl)-phenyl]-acetamide;
cyclohexanecarboxylic acid [2-methy 1-4-(2S-methyl-[1,3'S]bipyrrolidinyl-1'-yl)-phenyl]-amide;
bicyclo[2.2.1]heptane-2-carboxylic acid [2-methyl-4-(2S-methyl-[1,3'S]bipyrrolidinyl-1'-yl)-phenyl]-amide;
tetrahydro-pyran-4-carboxylic acid [2-methyl-4-(2(2S)-methyl-[1,3'(3'S)]bipyrrolidinyl-1'-yl)-phenyl]-amide;
tetrahydro-pyran-4-carboxylic acid [4-(2-methyl-[1,3']bipyrrolidinyl-1'-yl)-phenyl]-amide;
furan-3-carboxylic acid [2-methyl-4-(2S-methyl-[1,3'S]bipyrrolidinyl-1'-yl)-phenyl]-amide;
3-methyl-isoxazole-5-carboxylic acid [2-methyl-4-(2S-methyl-[1,3'S]bipyrrolidinyl-1'-yl)-phenyl]-amide;
3,5-dimethyl-isoxazole-4-carboxylic acid [2-methyl-4-(2(2S)-methyl-[1,3'(3'S)]bipyrrolidinyl-1'-yl)-phenyl]-amide; and
3,5-dimethyl-isoxazole-4-carboxylic acid [3-methyl-4-(2-methyl-[1,3']bipyrrolidinyl-1'-yl)-phenyl]-amide;
or a pharmaceutically acceptable salt thereof.

10. The compound of claim 1 selected from the group consisting of:
cyclohexanecarboxylic acid [2-methyl-4-(2S-methyl-[1,3'S]bipyrrolidinyl-1'-yl)-phenyl]-amide;
bicyclo[2.2.1]heptane-2-carboxylic acid [2-methyl-4-(2S-methyl-[1,3'S]bipyrrolidinyl-1'-yl)-phenyl]-amide;
tetrahydro-pyran-4-carboxylic acid [2-methyl-4-(2(2S)-methyl-[1,3'(3'S)]bipyrrolidinyl-1'-yl)-phenyl]-amide; and
3,5-dimethyl-isoxazole-4-carboxylic acid [2-methyl-4-(2(2S)-methyl-[1,3'(3'S)]bipyrrolidinyl-1'-yl)-phenyl]-amide;
or a pharmaceutically acceptable salt thereof.

11. The compound according or claim 1 which is having the formula (II):

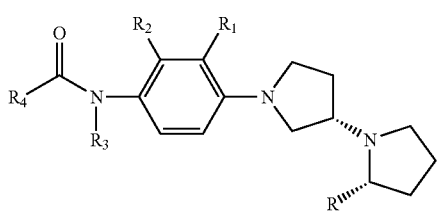

(II)

wherein R, R₁, R₂, R₃ and R₄ are as defined in claim 1.

12. A pharmaceutical composition comprising a compound of formula (I):

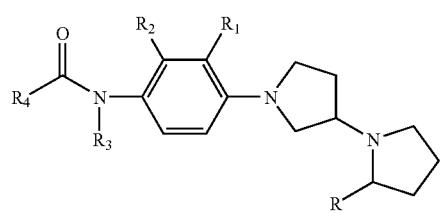

(I)

wherein
R, R₁, R₂ and R₃ are the same or different and independently of each other chosen from hydrogen, ($C_1$-$C_4$) alkyl or $CF_3$;
R₄ is selected from the group consisting of cyclopropyl, cyclopentyl, cyclohexyl, bicyclo[2,2,1]heptyl, cyclopentylmethyl, tetrahydropyranyl, furanyl, isoxazolyl and pyrazolyl; wherein said R₄ is optionally substituted one or more times with a substituent selected from halogen, methyl, ethyl, pyridinyl, 2-oxo-2H-pyridin-1-yl and $CF_3$; or
a pharmaceutically acceptable salt thereof or an enantiomer or a diastereomer thereof in combination with at least one pharmaceutically acceptable excipient, diluent or a carrier.

13. The composition according to claim 12, wherein R is methyl; R₂ is methyl or $CF_3$; R₁ and R₃ are hydrogen.

14. The composition according to claim 12, wherein R and R₁ are methyl; R₂ and R₃ are hydrogen.

15. The composition according to claim 12, wherein R₄ is selected from cyclopropyl, cyclopentyl, cyclohexyl or bicyclo[2.2.1]heptane.

16. The composition according to claim 12, wherein R₄ is tetrahydropyranyl.

17. The composition according to claim 12, wherein R₄ is selected from furanyl, isoxazolyl and pyrazolyl, which are optionally substituted one or more times with methyl.

18. The composition according to claim 12, wherein R₄ is selected from isoxazolyl or isoxazolyl substituted one or more times with methyl.

19. The composition according to claim 12, wherein the compound is selected from the group consisting of:
cyclopropanecarboxylic acid [2-methyl-4-(2-methyl-[1,3']bipyrrolidinyl-1'-yl)-phenyl]-amide;
cyclopropanecarboxylic acid [4-(2-methyl-[1,3']bipyrrolidinyl-1'-yl)-2-trifluoromethyl-phenyl]-amide;
cyclopropanecarboxylic acid [4-(2-methyl-[1,3']bipyrrolidinyl-1'-yl)-phenyl]-amide;
cyclopropanecarboxylic acid [3-methyl-4-(2-methyl-[1,3']bipyrrolidinyl-1'-yl)-phenyl]-amide;
2,2,3,3-tetramethyl-cyclopropanecarboxylic acid [2-methyl-4-(2(S)-methyl-[1,3'(S)]bipyrrolidinyl-1'-yl)-phenyl]-amide;
2,2,3,3-tetramethyl-cyclopropanecarboxylic acid [2-methyl-4-(2-methyl-[1,3']bipyrrolidinyl-1'-yl)-phenyl]-amide;
2,2,3,3-tetramethyl-cyclopropanecarboxylic acid [4-(2-methyl-[1,3']bipyrrolidinyl-1'-yl)-phenyl]-amide;
2,2,3,3-tetramethyl-cyclopropanecarboxylic acid [3-methyl-4-(2-methyl-[1,3']bipyrrolidinyl-1'-yl)-phenyl]-amide;
cyclopentanecarboxylic acid [2-methyl-4-(2(S)-methyl-[1,3'(S)]bipyrrolidinyl-1'-yl)-phenyl]-amide;
cyclohexanecarboxylic acid [2-methyl-4-(2S-methyl-[1,3'S]bipyrrolidinyl-1'-yl)-phenyl]-amide;
2-cyclopentyl-N-[2-methyl-4-(2-methyl-[1,3']bipyrrolidinyl-1'-yl)-phenyl]-acetamide;
2-cyclopentyl-N-[2-methyl-4-(2(S)-methyl-[1,3'(S)]bipyrrolidinyl-1'-yl)-phenyl]-acetamide;
2-cyclopentyl-N-[4-(2-methyl-[1,3']bipyrrolidinyl-1'-yl)-phenyl]-acetamide;
2-cyclopentyl-N-[3-methyl-4-(2-methyl-[1,3']bipyrrolidinyl-1'-yl)-phenyl]-acetamide;
bicyclo[2.2.1]heptane-2-carboxylic acid [2-methyl-4-(2S-methyl-[1,3'S]bipyrrolidinyl-1'-yl)-phenyl]-amide;
(1S,4R)-bicyclo[2.2.1]heptane-2-carboxylic acid [2-methyl-4-(2-methyl-[1,3']bipyrrolidinyl-1'-yl)-phenyl]-amide;
(1S,4R)-bicyclo[2.2.1]heptane-2-carboxylic acid [3-methyl-4-(2-methyl-[1,3']bipyrrolidinyl-1'-yl)-phenyl]-amide;
(1S,4R)-bicyclo[2.2.1]heptane-2-carboxylic acid [4-(2-methyl-[1,3']bipyrrolidinyl-1'-yl)-phenyl]-amide;
tetrahydro-pyran-4-carboxylic acid [2-methyl-4-(2(2S)-methyl-[1,3'(3'S)]bipyrrolidinyl-1'-yl)-phenyl]-amide;
tetrahydro-pyran-4-carboxylic acid [4-(2-methyl-[1,3']bipyrrolidinyl-1'-yl)-phenyl]-amide;
tetrahydro-pyran-4-carboxylic acid [3-methyl-4-(2-methyl-[1,3']bipyrrolidinyl-1'-yl)-phenyl]-amide;
tetrahydro-pyran-4-carboxylic acid [2-methyl-4-(2-methyl-[1,3']bipyrrolidinyl-1'-yl)-phenyl]-amide;
furan-3-carboxylic acid [2-methyl-4-(2S-methyl-[1,3'S]bipyrrolidinyl-1'-yl)-phenyl]-amide;
furan-2-carboxylic acid [2-methyl-4-(2(S)-methyl-[1,3'(S)]bipyrrolidinyl-1'-yl)-phenyl]-amide;
5-(2-oxo-2H-pyridin-1-yl)-furan-2-carboxylic acid [2-methyl-4-(2-methyl-[1,3']bipyrrolidinyl-1'-yl)-phenyl]-amide;
2-methyl-oxazole-4-carboxylic acid [2-methyl-4-(2(S)-methyl-[1,3'(S)]bipyrrolidinyl-1'-yl)-phenyl]-amide;
3-methyl-isoxazole-5-carboxylic acid [2-methyl-4-(2S-methyl-[1,3'S]bipyrrolidinyl-1'-yl)-phenyl]-amide;
3,5-dimethyl-isoxazole-4-carboxylic acid [2-methyl-4-(2(2S)-methyl-[1,3'(3'S)]bipyrrolidinyl-1'-yl)-phenyl]-amide;
3,5-dimethyl-isoxazole-4-carboxylic acid [3-methyl-4-(2-methyl-[1,3']bipyrrolidinyl-1'-yl)-phenyl]-amide;
3,5-dimethyl-isoxazole-4-carboxylic acid [2-methyl-4-(2-methyl-[1,3']bipyrrolidinyl-1'-yl)-phenyl]-amide;
3,5-dimethyl-isoxazole-4-carboxylic acid [4-(2-methyl-[1,3']bipyrrolidinyl-1'-yl)-phenyl]-amide;
1H-pyrazole-4-carboxylic acid [4-(2-methyl-[1,3']bipyrrolidinyl-1'-yl)-phenyl]-amide;
1H-pyrazole-4-carboxylic acid [2-methyl-4-(2-methyl-[1,3']bipyrrolidinyl-1'-yl)-phenyl]-amide;
1H-pyrazole-4-carboxylic acid [3-methyl-4-(2-methyl-[1,3']bipyrrolidinyl-1'-yl)-phenyl]-amide;

5-methyl-1H-pyrazole-3-carboxylic acid [2-methyl-4-(2 (2S)-methyl-[1,3'(3'S)]bipyrrolidinyl-1'-yl)-phenyl]-amide;

5-methyl-1H-pyrazole-3-carboxylic acid [2-methyl-4-(2-methyl-[1,3']bipyrrolidinyl-1'-yl)-phenyl]-amide;

5-methyl-1H-pyrazole-3-carboxylic acid [3-methyl-4-(2-methyl-[1,3']bipyrrolidinyl-1'-yl)-phenyl]-amide;

5-methyl-1H-pyrazole-3-carboxylic acid [4-(2-methyl-[1,3']bipyrrolidinyl-1'-yl)-phenyl]-amide;

5-methyl-1H-pyrazole-3-carboxylic acid [4-(2-methyl-[1,3']bipyrrolidinyl-1'-yl)-2-trifluoromethyl-phenyl]-amide;

1,5-dimethyl-1H-pyrazole-3-carboxylic acid [2-methyl-4-(2(2S)-methyl-[1,3'(3'S)]bipyrrolidinyl-1'-yl)-phenyl]-amide; and 5-pyridin-4-yl-2H-pyrazole-3-carboxylic acid [2-methyl-4-(2-methyl-[1,3']bipyrrolidinyl-1'-yl)-phenyl]-amide;

or a pharmaceutically acceptable salt thereof.

20. The composition according to claim 12, wherein the compound is selected from the group consisting of:

cyclopropanecarboxylic acid [2-methyl-4-(2-methyl-[1,3']bipyrrolidinyl-1'-yl)-phenyl]-amide;

2-cyclopentyl-N-[2-methyl-4-(2-methyl-[1,3']bipyrrolidinyl-1'-yl)-phenyl]-acetamide;

cyclohexanecarboxylic acid [2-methyl-4-(2S-methyl-[1,3'S]bipyrrolidinyl-1'-yl)-phenyl]-amide;

bicyclo[2.2.1]heptane-2-carboxylic acid [2-methyl-4-(2S-methyl-[1,3'S]bipyrrolidinyl-1'-yl)-phenyl]-amide;

tetrahydro-pyran-4-carboxylic acid [2-methyl-4-(2(2S)-methyl-[1,3'(3'S)]bipyrrolidinyl-1'-yl)-phenyl]-amide;

tetrahydro-pyran-4-carboxylic acid [4-(2-methyl-[1,3']bipyrrolidinyl-1'-yl)-phenyl]-amide;

furan-3-carboxylic acid [2-methyl-4-(2S-methyl-[1,3'S]bipyrrolidinyl-1'-yl)-phenyl]-amide;

3-methyl-isoxazole-5-carboxylic acid [2-methyl-4-(2S-methyl-[1,3'S]bipyrrolidinyl-1'-yl)-phenyl]-amide;

3,5-dimethyl-isoxazole-4-carboxylic acid [2-methyl-4-(2 (2S)-methyl-[1,3'(3'S)]bipyrrolidinyl-1'-yl)-phenyl]-amide; and 3,5-dimethyl-isoxazole-4-carboxylic acid [3-methyl-4-(2-methyl-[1,3']bipyrrolidinyl-1'-yl)-phenyl]-amide;

or a pharmaceutically acceptable salt thereof.

21. The composition according to claim 12, wherein the compound is selected from the group consisting of:

cyclohexanecarboxylic acid [2-methyl-4-(2S-methyl-[1,3'S]bipyrrolidinyl-1'-yl)-phenyl]-amide;

bicyclo[2.2.1]heptane-2-carboxylic acid [2-methyl-4-(2S-methyl-[1,3'S]bipyrrolidinyl-1'-yl)-phenyl]-amide;

tetrahydro-pyran-4-carboxylic acid [2-methyl-4-(2(2S)-methyl-[1,3'(3'S)]bipyrrolidinyl-1'-yl)-phenyl]-amide; and 3,5-dimethyl-isoxazole-4-carboxylic acid [2-methyl-4-(2 (2S)-methyl-[1,3'(3'S)]bipyrrolidinyl-1'-yl)-phenyl]-amide;

or a pharmaceutically acceptable salt thereof.

22. The composition according to claim 12, wherein the compound is having the formula (II):

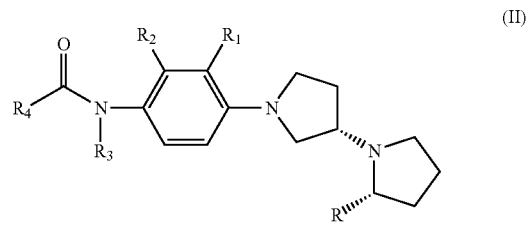

(II)

wherein R, $R_1$, $R_2$, $R_3$ and $R_4$ are as defined in claim 12.

23. A method of treating a disease in a patient, said disease selected from the group consisting of a sleep related disorder selected from the group consisting of narcolepsy, circadian rhythm sleep disorder, obstructive sleep apnea, periodic limb movement and restless leg syndrome, excessive sleepiness and drowsiness due to medication side-effect; and depression, comprising administering to said patient a therapeutically effective amount of a compound of formula (I):

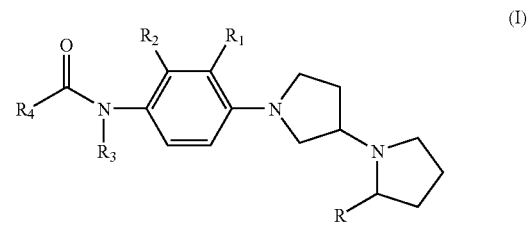

(I)

wherein

R, $R_1$, $R_2$ and $R_3$ are the same or different and independently of each other chosen from hydrogen, ($C_1$-$C_4$) alkyl or $CF_3$;

$R_4$ is selected from the group consisting of cyclopropyl, cyclopentyl, cyclohexyl, bicyclo[2,2,1]heptyl, cyclopentylmethyl, tetrahydropyranyl, furanyl, 2-, 4- or 5-oxazolyl, 3-, 4- or 5-isoxazolyl and 3-, 4- or 5-pyrazolyl; wherein said $R_4$ is optionally substituted one or more times with a substituent selected from halogen, methyl, ethyl, pyridinyl, 2-oxo-2H-pyridin-1-yl and $CF_3$; or a pharmaceutically acceptable salt thereof or an enantiomer or a diastereomer thereof optionally in combination with one or more pharmaceutically acceptable excipient, diluent or a carrier.

24. The method according to claim 23, wherein the sleep disorder is narcolepsy.

25. The method according to claim 23, wherein the disease is depression.

26. The method according to claim 23, wherein the compound is selected from the group consisting of:

cyclopropanecarboxylic acid [2-methyl-4-(2-methyl-[1,3']bipyrrolidinyl-1'-yl)-phenyl]-amide;

cyclopropanecarboxylic acid [4-(2-methyl-[1,3']bipyrrolidinyl-1'-yl)-2-trifluoromethyl-phenyl]-amide;

cyclopropanecarboxylic acid [4-(2-methyl-[1,3']bipyrrolidinyl-1'-yl)-phenyl]-amide;

cyclopropanecarboxylic acid [3-methyl-4-(2-methyl-[1,3']bipyrrolidinyl-1'-yl)-phenyl]-amide;

2,2,3,3-tetramethyl-cyclopropanecarboxylic acid [2-methyl-4-(2(S)-methyl-[1,3'(S)]bipyrrolidinyl-1'-yl)-phenyl]-amide;

2,2,3,3-tetramethyl-cyclopropanecarboxylic acid [2-methyl-4-(2-methyl-[1,3']bipyrrolidinyl-1'-yl)-phenyl]-amide;

2,2,3,3-tetramethyl-cyclopropanecarboxylic acid [4-(2-methyl-[1,3']bipyrrolidinyl-1'-yl)-phenyl]-amide;
2,2,3,3-tetramethyl-cyclopropanecarboxylic acid [3-methyl-4-(2-methyl-[1,3']bipyrrolidinyl-1'-yl)-phenyl]-amide;
cyclopentanecarboxylic acid [2-methyl-4-(2(S)-methyl-[1,3'(S)]bipyrrolidinyl-1'-yl)-phenyl]-amide;
cyclohexanecarboxylic acid [2-methyl-4-(2S-methyl-[1,3'S]bipyrrolidinyl-1'-yl)-phenyl]-amide;
2-cyclopentyl-N-[2-methyl-4-(2-methyl-[1,3']bipyrrolidinyl-1'-yl)-phenyl]-acetamide;
2-cyclopentyl-N-[2-methyl-4-(2(S)-methyl-[1,3'(S)]bipyrrolidinyl-1'-yl)-phenyl]-acetamide;
2-cyclopentyl-N-[4-(2-methyl-[1,3']bipyrrolidinyl-1'-yl)-phenyl]-acetamide;
2-cyclopentyl-N-[3-methyl-4-(2-methyl-[1,3']bipyrrolidinyl-1'-yl)-phenyl]-acetamide;
bicyclo[2.2.1]heptane-2-carboxylic acid [2-methyl-4-(2S-methyl-[1,3'S]bipyrrolidinyl-1'-yl)-phenyl]-amide;
(1S,4R)-bicyclo[2.2.1]heptane-2-carboxylic acid [2-methyl-4-(2-methyl-[1,3']bipyrrolidinyl-1'-yl)-phenyl]-amide;
(1S,4R)-bicyclo[2.2.1]heptane-2-carboxylic acid [3-methyl-4-(2-methyl-[1,3']bipyrrolidinyl-1'-yl)-phenyl]-amide;
(1S,4R)-bicyclo[2.2.1]heptane-2-carboxylic acid [4-(2-methyl-[1,3']bipyrrolidinyl-1'-yl)-phenyl]-amide;
tetrahydro-pyran-4-carboxylic acid [2-methyl-4-(2(2S)-methyl-[1,3'(3'S)]bipyrrolidinyl-1'-yl)-phenyl]-amide;
tetrahydro-pyran-4-carboxylic acid [4-(2-methyl-[1,3']bipyrrolidinyl-1'-yl)-phenyl]-amide;
tetrahydro-pyran-4-carboxylic acid [3-methyl-4-(2-methyl-[1,3']bipyrrolidinyl-1'-yl)-phenyl]-amide;
tetrahydro-pyran-4-carboxylic acid [2-methyl-4-(2-methyl-[1,3']bipyrrolidinyl-1'-yl)-phenyl]-amide;
furan-3-carboxylic acid [2-methyl-4-(2S-methyl-[1,3'S]bipyrrolidinyl-1'-yl)-phenyl]-amide;
furan-2-carboxylic acid [2-methyl-4-(2(S)-methyl-[1,3'(S)]bipyrrolidinyl-1'-yl)-phenyl]-amide;
5-(2-oxo-2H-pyridin-1-yl)-furan-2-carboxylic acid [2-methyl-4-(2-methyl-[1,3']bipyrrolidinyl-1'-yl)-phenyl]-amide;
2-methyl-oxazole-4-carboxylic acid [2-methyl-4-(2(S)-methyl-[1,3'(S)]bipyrrolidinyl-1'-yl)-phenyl]-amide;
3-methyl-isoxazole-5-carboxylic acid [2-methyl-4-(2S-methyl-[1,3'S]bipyrrolidinyl-1'-yl)-phenyl]-amide;
3,5-dimethyl-isoxazole-4-carboxylic acid [2-methyl-4-(2(2S)-methyl-[1,3'(3'S)]bipyrrolidinyl-1'-yl)-phenyl]-amide;
3,5-dimethyl-isoxazole-4-carboxylic acid [3-methyl-4-(2-methyl-[1,3']bipyrrolidinyl-1'-yl)-phenyl]-amide;
3,5-dimethyl-isoxazole-4-carboxylic acid [2-methyl-4-(2-methyl-[1,3']bipyrrolidinyl-1'-yl)-phenyl]-amide;
3,5-dimethyl-isoxazole-4-carboxylic acid [4-(2-methyl-[1,3']bipyrrolidinyl-1'-yl)-phenyl]-amide;
1H-pyrazole-4-carboxylic acid [4-(2-methyl-[1,3']bipyrrolidinyl-1'-yl)-phenyl]-amide;
1H-pyrazole-4-carboxylic acid [2-methyl-4-(2-methyl-[1,3']bipyrrolidinyl-1'-yl)-phenyl]-amide;
1H-pyrazole-4-carboxylic acid [3-methyl-4-(2-methyl-[1,3']bipyrrolidinyl-1'-yl)-phenyl]-amide;
5-methyl-1H-pyrazole-3-carboxylic acid [2-methyl-4-(2(2S)-methyl-[1,3'(3'S)]bipyrrolidinyl-1'-yl)-phenyl]-amide;
5-methyl-1H-pyrazole-3-carboxylic acid [2-methyl-4-(2-methyl-[1,3']bipyrrolidinyl-1'-yl)-phenyl]-amide;
5-methyl-1H-pyrazole-3-carboxylic acid [3-methyl-4-(2-methyl-[1,3']bipyrrolidinyl-1'-yl)-phenyl]-amide;
5-methyl-1H-pyrazole-3-carboxylic acid [4-(2-methyl-[1,3']bipyrrolidinyl-1'-yl)-phenyl]-amide;
5-methyl-1H-pyrazole-3-carboxylic acid [4-(2-methyl-[1,3']bipyrrolidinyl-1'-yl)-2-trifluoromethyl-phenyl]-amide;
1,5-dimethyl-1H-pyrazole-3-carboxylic acid [2-methyl-4-(2(2S)-methyl-[1,3'(3'S)]bipyrrolidinyl-1'-yl)-phenyl]-amide; and
5-pyridin-4-yl-2H-pyrazole-3-carboxylic acid [2-methyl-4-(2-methyl-[1,3']bipyrrolidinyl-1'-yl)-phenyl]-amide;
or a pharmaceutically acceptable salt thereof.

27. The method according to claim 23, wherein the compound is selected from the group consisting of:
cyclopropanecarboxylic acid [2-methyl-4-(2-methyl-[1,3']bipyrrolidinyl-1'-yl)-phenyl]-amide;
2-cyclopentyl-N-[2-methyl-4-(2-methyl-[1,3']bipyrrolidinyl-1'-yl)-phenyl]-acetamide;
cyclohexanecarboxylic acid [2-methy 1-4-(2S-methyl-[1,3'S]bipyrrolidinyl-1'-yl)-phenyl]-amide;
bicyclo[2.2.1]heptane-2-carboxylic acid [2-methyl-4-(2S-methyl-[1,3'S]bipyrrolidinyl-1'-yl)-phenyl]-amide;
tetrahydro-pyran-4-carboxylic acid [2-methyl-4-(2(2S)-methyl-[1,3'(3'S)]bipyrrolidinyl-1'-yl)-phenyl]-amide;
tetrahydro-pyran-4-carboxylic acid [4-(2-methyl-[1,3']bipyrrolidinyl-1'-yl)-phenyl]-amide;
furan-3-carboxylic acid [2-methyl-4-(2S-methyl-[1,3'S]bipyrrolidinyl-1'-yl)-phenyl]-amide;
3-methyl-isoxazole-5-carboxylic acid [2-methyl-4-(2S-methyl-[1,3'S]bipyrrolidinyl-1'-yl)-phenyl]-amide;
3,5-dimethyl-isoxazole-4-carboxylic acid [2-methyl-4-(2(2S)-methyl-[1,3'(3'S)]bipyrrolidinyl-1'-yl)-phenyl]-amide; and
3,5-dimethyl-isoxazole-4-carboxylic acid [3-methyl-4-(2-methyl-[1,3']bipyrrolidinyl-1'-yl)-phenyl]-amide;
or a pharmaceutically acceptable salt thereof.

28. The method according to claim 23, wherein the compound is selected from the group consisting of:
cyclohexanecarboxylic acid [2-methyl-4-(2S-methyl-[1,3'S]bipyrrolidinyl-1'-yl)-phenyl]-amide;
bicyclo[2.2.1]heptane-2-carboxylic acid [2-methyl-4-(2S-methyl-[1,3'S]bipyrrolidinyl-1'-yl)-phenyl]-amide;
tetrahydro-pyran-4-carboxylic acid [2-methyl-4-(2(2S)-methyl-[1,3'(3'S)]bipyrrolidinyl-1'-yl)-phenyl]-amide; and
3,5-dimethyl-isoxazole-4-carboxylic acid [2-methyl-4-(2(2S)-methyl-[1,3'(3'S)]bipyrrolidinyl-1'-yl)-phenyl]-amide;
or a pharmaceutically acceptable salt thereof.

29. The method according to claim 23, wherein the compound is having the formula (II):

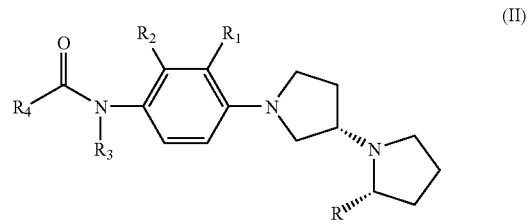

(II)

wherein R, $R_1$, $R_2$, $R_3$ and $R_4$ are as defined in claim 23.

* * * * *

UNITED STATES PATENT AND TRADEMARK OFFICE
CERTIFICATE OF CORRECTION

| | | |
|---|---|---|
| PATENT NO. | : 8,088,808 B2 | Page 1 of 1 |
| APPLICATION NO. | : 12/724028 | |
| DATED | : January 3, 2012 | |
| INVENTOR(S) | : Werngard Czechtizky et al. | |

It is certified that error appears in the above-identified patent and that said Letters Patent is hereby corrected as shown below:

In column 16, line 10, delete ""gmole"" and insert -- "µmole" --, therefor.

In column 16, line 65, delete "min" and insert -- mm --, therefor.

In column 33, line 6, delete "Cyclopropane carboxylic" and insert -- Cyclopropanecarboxylic --, therefor.

In column 43, line 24, delete "cyclop entyl" and insert -- cyclopentyl --, therefor.

In column 43, line 30, delete "Cyclopentane carboxylic" and insert -- Cyclopentanecarboxylic --, therefor.

In column 45, line 40, after "Test Compounds" insert -- : --.

In column 45, line 51, after "blanks" insert -- . --.

In column 47, line 54, after "training" insert -- . --.

In column 49, line 20, in claim 8, delete "methy 1" and insert -- methyl --, therefor.

In column 50, line 33, in claim 9, delete "methy 1" and insert -- methyl --, therefor.

In column 50, line 66, in claim 11, delete "or" and insert -- to --, therefor.

In column 56, line 20, in claim 27, delete "methy 1" and insert -- methyl --, therefor.

Signed and Sealed this
Third Day of July, 2012

David J. Kappos
*Director of the United States Patent and Trademark Office*